(12) United States Patent
Dunaway et al.

(10) Patent No.: US 12,414,906 B2
(45) Date of Patent: *Sep. 16, 2025

(54) COMPOSITIONS AND METHODS FOR TREATING HOT FLASHES

(71) Applicant: The Procter & Gamble Company, Cincinnati, OH (US)

(72) Inventors: Connie Michelle Dunaway, West Chester, OH (US); Samantha Chen-Yee Wang, Cincinnati, OH (US); Mary Jane Watson, Cincinnati, OH (US); Matthew Lawrence Lynch, Mariemont, OH (US); Jamie Lynn Dria, Deerfield Township, OH (US); Brandon Philip Illie, Felicity, OH (US); Taotao Zhu, West Chester, OH (US); Dorothy Angela Hall, Blanchester, OH (US); Beth Ann Schubert, Maineville, OH (US)

(73) Assignee: The Procter & Gamble Company, Cincinnati, OH (US)

(\*) Notice: Subject to any disclaimer, the term of this patent is extended or adjusted under 35 U.S.C. 154(b) by 14 days.

This patent is subject to a terminal disclaimer.

(21) Appl. No.: 17/962,763

(22) Filed: Oct. 10, 2022

(65) Prior Publication Data

US 2023/0050077 A1 Feb. 16, 2023

Related U.S. Application Data

(63) Continuation of application No. PCT/US2021/026359, filed on Apr. 8, 2021.

(Continued)

(51) Int. Cl.
*A61K 8/49* (2006.01)
*A61K 8/02* (2006.01)
(Continued)

(52) U.S. Cl.
CPC .............. *A61K 8/4973* (2013.01); *A61K 8/34* (2013.01); *A61K 8/37* (2013.01); *A61K 31/23* (2013.01);
(Continued)

(58) Field of Classification Search
None
See application file for complete search history.

(56) References Cited

U.S. PATENT DOCUMENTS 4,252,789 A 2/1981 Broad
4,322,400 A 3/1982 Yuhas
(Continued)

FOREIGN PATENT DOCUMENTS

EP 2465487 A2 6/2012
JP 2004161622 A 6/2004
(Continued)

OTHER PUBLICATIONS

PCT Search Report and Written Opinion for PCT/US2021/026359 dated Jul. 26, 2021, 12 pages.
(Continued)

*Primary Examiner* — Kyung S Chang
(74) *Attorney, Agent, or Firm* — Anna E. Haller

(57) ABSTRACT

The present disclosure relates to compositions comprising an aqueous solution of at least about 70% by weight water in combination with selected fatty acid salts and optionally an alcohol and/or a cooling sensate, as well as methods of using the same to treat symptoms of hot flashes. The fatty acid salts form fiber-like crystalline particles that together form a self-supporting mesh structure with voids, the aqueous solution being contained in the voids. When the composition is compressed above a critical stress, the mesh allows for the entrapped aqueous solution to be expressed.

18 Claims, 2 Drawing Sheets

Related U.S. Application Data

(60) Provisional application No. 63/007,965, filed on Apr. 10, 2020, provisional application No. 63/007,973, filed on Apr. 10, 2020, provisional application No. 63/007,967, filed on Apr. 10, 2020, provisional application No. 63/007,972, filed on Apr. 10, 2020.

(51) Int. Cl.

| | |
|---|---|
| *A61K 8/20* | (2006.01) |
| *A61K 8/34* | (2006.01) |
| *A61K 8/36* | (2006.01) |
| *A61K 8/37* | (2006.01) |
| *A61K 8/73* | (2006.01) |
| *A61K 8/92* | (2006.01) |
| *A61K 31/16* | (2006.01) |
| *A61K 31/20* | (2006.01) |
| *A61K 31/22* | (2006.01) |
| *A61K 31/23* | (2006.01) |
| *A61K 45/06* | (2006.01) |
| *A61P 43/00* | (2006.01) |
| *A61Q 19/00* | (2006.01) |

(52) U.S. Cl.
CPC .............. *A61P 43/00* (2018.01); *A61Q 19/00* (2013.01); *A61K 2800/10* (2013.01)

(56) References Cited

U.S. PATENT DOCUMENTS

| | | | |
|---|---|---|---|
| 5,340,492 | A | 8/1994 | Kacher et al. |
| 5,425,892 | A | 6/1995 | Taneri et al. |
| 5,552,136 | A | 9/1996 | Motley |
| 6,365,567 | B1 | 4/2002 | Nadakatti et al. |
| 9,622,943 | B2 | 4/2017 | Scala et al. |
| 9,962,320 | B2 | 5/2018 | Kim |
| 2012/0100223 | A1* | 4/2012 | Bhagat .................... A61P 15/08 424/771 |
| 2013/0202668 | A1 | 8/2013 | Prost et al. |
| 2013/0225472 | A1 | 8/2013 | Wu et al. |
| 2018/0066210 | A1 | 3/2018 | Frankenbach et al. |
| 2018/0273517 | A1* | 9/2018 | Patron .................. A61K 9/0014 |

FOREIGN PATENT DOCUMENTS

| | | |
|---|---|---|
| WO | 0045815 A1 | 8/2000 |
| WO | 2002013776 A2 | 2/2002 |
| WO | 2009046008 A2 | 4/2009 |
| WO | 2012129722 A1 | 10/2012 |
| WO | 2019017735 A2 | 1/2019 |
| WO | 2019182198 A1 | 9/2019 |

OTHER PUBLICATIONS

Clan Beauty by Found, Cucumber Cooling Stick, Year—Not Known, pp. 02.
Constantinos V. Nikiforidis et al., "Organogel formation via supramolecular assembly of oleic acid and sodium oleate", RSC Adv., Year 2015, 5, pp. 47466-47475.
Jingmei Liang et al., "Solvent-Induced Crystal Morphology Transformation in a Ternary Soap System: Sodium Stearate Crystalline Fibers and Platelets", Langmuir Year 2001, 17, pp. 6447-6454.
Lynch et al., "Intermolecular Interactions and the Structure of Fatty Acid-Soap Crystals", J. Phys. Chem. B 105, Year 2001, pp. 552-561.
Lynch et al., "Spectroscopic and thermal characterization of 1:2 sodium soap/ fatty acid, Acid soap crystals", J. Phys. Chem. 100, Year 1996, pp. 357-361.
Lynch, "Acid-Soaps", Current Opinion in Colloid and Interface Science 2, Year 1997, pp. 495-500.
Makeup Alley; "Hard Candy Sheer Envy Coconut Water Primer Stick", Retrieved from internet, Year—Not Known, pp. 2.
Marc N.G. de Mul et al., "Solution Phase Behavior and Solid Phase Structure of Long-chain Sodium Soap Mixtures", Langmuir Year 2000, 16, pp. 8276-8284.
Milk Makeup, Cooling Water Eye Gel Stick for Puffy Eyes, Retrieved from internet, Year—Not known, pp. 5.
Musings of a muse, "Skin Food Facial Ice Vita Cooling Stick Review", URL: https://www.musingsofamuse.com, Year 2013, 05, pp. 15.
Pink Lotus Elements "Menopause Chill Out Spray—Refreshing & Pure Essential Oils", Retrieved from internet, Year—Not Known,, pp. 6.

* cited by examiner

COMPOSITIONS AND METHODS FOR TREATING HOT FLASHES

FIELD OF THE INVENTION

The present disclosure relates to compositions comprising an aqueous solution of at least about 70% by weight water in combination with selected fatty acid salts and optionally an alcohol and/or a cooling sensate, as well as methods of using the same to treat symptoms of hot flashes. The fatty acid salts form fiber-like crystalline particles that together form a self-supporting mesh structure with voids, the aqueous solution being contained in the voids. When the composition is compressed above a critical stress, the mesh allows for the entrapped aqueous solution to be expressed.

BACKGROUND OF THE INVENTION

Estimates indicate that by 2030 there will be about 1.2 billion menopausal and post-menopausal women in the world. As such, there is increasing concern surrounding the conditions and symptoms experienced by perimenopausal, menopausal, post-menopausal women, and the need for treatment therefore is growing as well. Menopause generally occurs 12 months after a woman's last menstrual period; however, it is considered a gradual process. Menopause is associated with a decrease in estrogen production and decreased estrogen levels may contribute to hot flashes or flushes, night sweats, mood changes, stress, fatigue, sleeping difficulties, sexual difficulties, mild depression, irritability, vaginal dryness, brain fog, and difficulty with memory.

Hot flashes are one of the most common symptoms of menopause. A hot flash starts with a sudden sensation of intense heat, often accompanied by sweating and blushing, followed by chills, as the body tries to compensate for the perceived heat. It is believed that hot flashes occur as a result of a decrease in estrogen levels and the subsequent release of hormones that affect the brain's thermostat. Hot flashes occur sporadically, but may be triggered by various stimuli, such as anxiety, stress, high environmental temperatures, caffeine, and alcohol. Hot flashes often occur during the night.

There are a variety of solutions that have been proposed to address the above-described symptoms, particularly hot flashes. These solutions range from very basic, do-it-yourself techniques, such as wearing layered clothing or briefly placing one's head in the freezer, to more complex remedies that require the support of a medical professional, e.g., prescription-based remedies. Prescription-based remedies have included hormone replacement therapy, which can include an estrogen supplement with or without progesterone. Hormone replacement therapy has also been reduced by contraindications, such as a history of cancer and thromboembolism. Prescription medications suggested for the relief of menopausal symptoms include clonidine and methyldopa, as well as anti-depressants, such as selective serotonin reuptake inhibitors (SSRIs), for example, Effexor XR® (commonly known as venlafaxine). These prescription medications suppress the release of norepinephrine, which is believed to activate the thermoregulatory centers of the brain. These prescription medications have had mixed success in clinical trials and may be accompanied by side effects, such as fatigue, weakness, dizziness and nausea. Different supplements for the relief of menopausal symptoms are also available in the market today and vary in effectiveness. These supplements typically contain vitamins, botanical ingredients, or other nutrients to help normalize hormone levels. Because the above treatments are orally administered, none of these treatments provide immediate relief, for example, during a hot flash.

Therefore, there remains a need for an alternative, non-medical solution to alleviate the symptoms associated with menopause, particularly hot flashes. There is a need for an effective remedy that is non-hormonal and does not require a doctor's prescription. There is a need for a remedy that can provide immediate relief of hot flashes. Surprisingly, it has been found that a composition comprising mostly water, a salt of a fatty acid, and, optionally, a sensate and/or an alcohol can provide immediate relief of hot flashes, when applied to the skin.

SUMMARY OF THE INVENTION

The present disclosure attempts to solve one more of the needs by providing a personal care composition comprising: i) from about 1% to about 12% by weight of a salt of a fatty acid containing from about 13 to about 20 carbon atoms, ii) from about 70% to about 99.5% by weight water, iii) from 0.5% to about 15% by weight of an alcohol selected from the group consisting of methanol, ethanol, propanol, isopropanol, and mixtures thereof, and iv) from about 0.1% to about 25% by weight of a sensate, preferably a cooling sensate.

The present disclosure also relates to a method of treating hot flashes, the method comprising the steps of: i) providing to a user in need thereof a composition comprising from about 0.01% to about 12% by weight of a salt of a fatty acid containing from about 13 to about 20 carbon atoms, ii) from about 70% to about 99.5% by weight water; iii) applying the composition to at least a portion of keratinous tissue of the user, where the keratinous tissue is skin or hair; and iv) optionally leaving the composition on the keratinous tissue for at least about 60 seconds.

BRIEF DESCRIPTION OF THE DRAWINGS

While the specification concludes with claims particularly pointing out and distinctly claiming the subject matter that is regarded as the present disclosure, it is believed that the disclosure will be more fully understood from the following description taken in conjunction with the accompanying drawings. Some of the figures may have been simplified by the omission of selected elements for the purpose of more clearly showing other elements. Such omissions of elements in some figures are not necessarily indicative of the presence or absence of particular elements in any of the exemplary embodiments, except as may be explicitly delineated in the corresponding written description. None of the drawings are necessarily to scale.

DETAILED DESCRIPTION OF THE INVENTION

Figure 1:
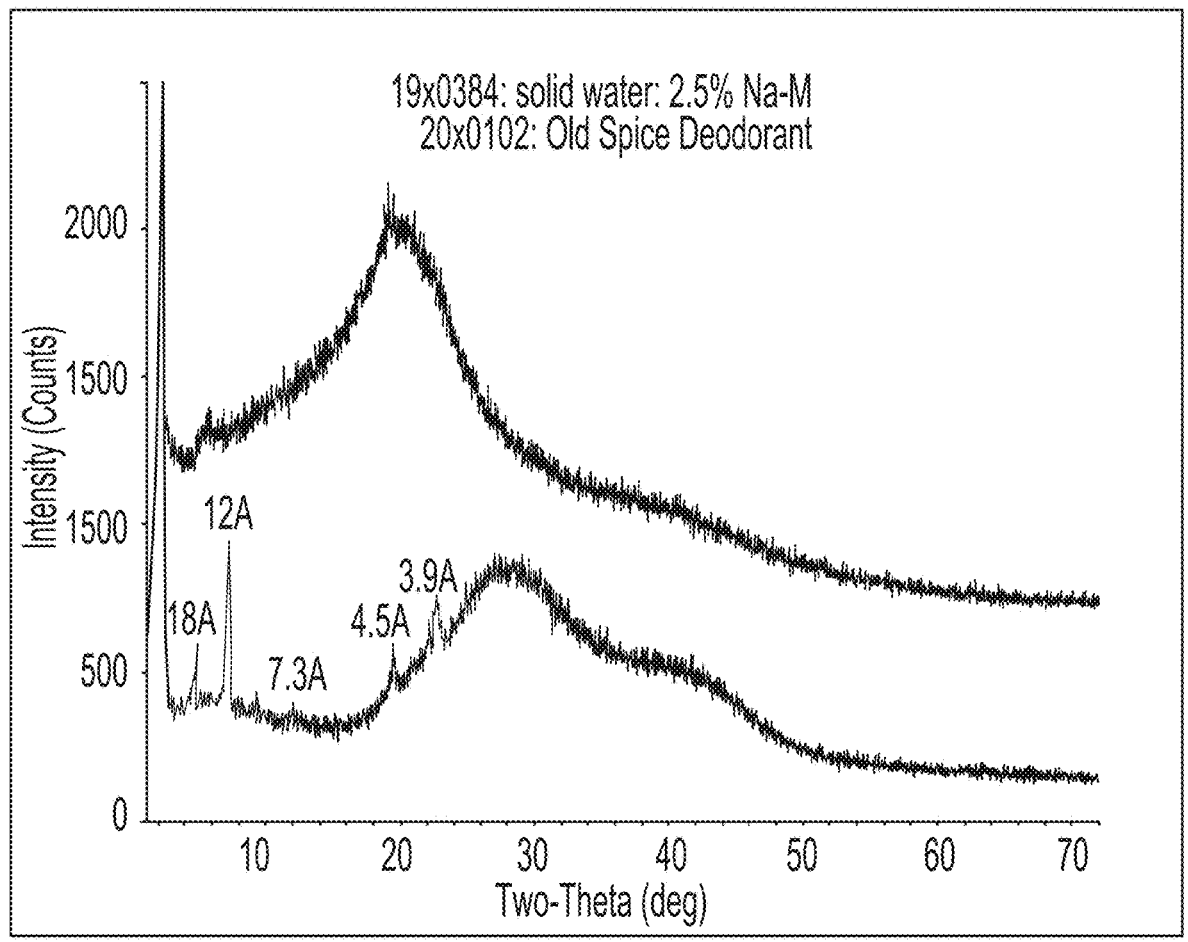
FIG. 1. X-ray Diffraction Pattern

While the specification concludes with claims particularly pointing out and distinctly claiming the subject matter of the present invention, it is believed that the invention can be more readily understood from the following description.

Various non-limiting embodiments of the present disclosure will now be described to provide an overall understanding of the principles of the compositions and methods disclosed herein. Those of ordinary skill in the art will understand that the embodiments and methods described herein are non-limiting example embodiments and that the scope of the present disclosure is defined solely by the claims. The features illustrated or described in connection with one non-limiting embodiment can be combined with the features of other non-limiting embodiments. Such modifications and variations are intended to be included within the scope of the present disclosure.

All percentages are by weight of the composition, unless specifically stated otherwise. All ratios are weight ratios, unless specifically stated otherwise. All ranges are inclusive of narrower ranges and combinable. Delineated upper and lower range limits are interchangeable to create further ranges not explicitly delineated. The number of significant digits conveys neither a limitation on the indicated amounts nor on the accuracy of the measurements. All numerical amounts are understood to be modified by the word "about" unless otherwise specifically indicated. Unless otherwise indicated, all measurements are understood to be made at approximately 25° C. and at ambient conditions, where "ambient conditions" means conditions under about 1 atmosphere of pressure and at about 50% relative humidity.

The compositions of the disclosure can comprise, consist essentially of, or consist of, the components as well as optional ingredients described herein. As used herein, "consisting essentially of" means that the composition or component may include additional ingredients or features, but only if the additional ingredients or features do not materially alter the basic and novel characteristics of the claimed compositions or methods. As used in the description and the appended claims, the singular forms "a," "an," and "the" are intended to include the plural forms as well, unless the context clearly indicates otherwise. Unless otherwise defined, all technical and scientific terms used herein have the same meaning as commonly understood by one of ordinary skill in the art to which this invention belongs.

As used herein, the terms "preferred", "preferably", and variants of these terms refer to examples of the invention that afford certain benefits, under certain circumstances. However, other examples may also be preferred, under the same or other circumstances. Furthermore, the recitation of one or more preferred examples does not imply that other examples are not useful, and is not intended to exclude other examples from the scope of the invention.

"Estrogen agent" means any natural or synthetic estrogen hormone (e.g., estrone, estradiol and estriol), metabolites thereof, esters thereof, analogues thereof, phytoestrogens (e.g., isoflavones, coumestans, prenylflavonoids), estrogen precursors (e.g., dehydroepiandrosterone) and/or any compound which binds to an estrogen receptor or which otherwise exhibits at least mild or weak estrogen-like effects, including selective estrogen receptor modulators ("SERM") such as, for example: afimoxifene (4-hydroxytamoxifen), arzoxifene, bazedoxifene, clomifene, femarelle (DT56a), lasofoxifene, ormeloxifene, raloxifene, tamoxifen, toremifene, mifepristone (RU486), VA2914, ulipristal, Proellex, Asoprisnil, and CDB-4124.

Menopause, in the absence of hormone replacement therapy or other medication, is a gradual process that a woman experiences and may comprise three stages: perimenopause stage or menopause transition, menopause stage, and postmenopause stage. As used herein, the term "menopause" is understood to mean one or more of these three stages. The menopause stage is the point when a woman no longer has menstrual periods. At this stage, the ovaries have stopped releasing eggs and producing most of their estrogen. The menopause stage is diagnosed when a woman has gone without a period for 12 consecutive months.

The terms menthol and menthyl, as used herein, include dextro- and levorotatory isomers of these compounds and racemic mixtures thereof.

A "perimenopausal" woman is one who in the absence of hormone replacement therapy or other medication would experience a change in her intermenstrual cycle interval and have associated symptoms of estrogen deficiency, such as vasomotor flushes, vaginal dryness and/or worsening premenstrual syndrome. Also included are women who in the absence of hormone replacement therapy or other medication would experience less than 12 months amenorrhea. Perimenopause may begin eight to ten years before menopause, when the ovaries gradually produce less estrogen. Perimenopause lasts up until menopause, the point when the ovaries stop releasing eggs. In the last one to two years of perimenopause, the drop in estrogen accelerates. Women who are still in perimenopause may experience some of the same symptoms as women who are in menopause.

"Pharmacologically effective amount", "therapeutically effective amount" or simply "effective amount" means the amount of a composition, or ingredient thereof, effective to produce the intended pharmacological, therapeutic, or preventive result.

The "postmenopause" stage comprises the years after menopause. During this stage, a woman, in the absence of hormone replacement therapy or other medication, may still experience menopausal symptoms, such as hot flashes, but these symptoms may ease.

"Progesterone agent" means any natural or synthetic progesterone hormone, metabolites thereof, analogues thereof, progesterone precursors and/or any compound which binds to a progesterone receptor or which otherwise exhibits at least mild or weak progesterone-like effects, including selective progesterone receptor modulators ("SPRM") such as, for example, telapristone.

"Substantially free" means a component or material is present in amount less than 0.1%, 0.05%, 0.025%, 0.01%, or 0.001% by weight of the composition.

The symptoms of menopause, particularly hot flashes, may be quite disruptive and may occur during perimenopause as well as postmenopause, woman suffering from these symptoms desire a remedy. Preferably, the remedy is an easy-to-use treatment that facilitates compliance. The treatment is also preferably discreet and practical in any situation, for example, for use at work or at home. Preferably, the treatment provides immediate relief of hot flashes.

Surprisingly, it has been found that a composition(s) comprising mostly water, a salt of a fatty acid, and, optionally, a sensate and/or an alcohol can provide immediate relief of hot flashes, when applied to the skin. The topical application of the composition(s) may also provide targeted cooling at the locations where a user feels the hottest, e.g., face, neck, chest, all without adding much moisture to already perspiring skin (in contrast with existing solutions, such as sprays) or leaving a residue on the skin (the composition also dries clear). Such targeted cooling may be preferred over existing treatments that require oral administration, such as drugs or supplements. Also in contrast to existing solutions, such as sprays, the composition(s) advantageously provides both an immediate, evaporative cooling and an extended cooling sensation. The extended cooling sensation may continue for about 10 seconds to about 60 minutes, or for about 10 seconds to about 30 minutes, or for about 10 seconds to about 20 minutes, or about 10 seconds to about 15 minutes. The average hot flash lasts from about 30 seconds to about 10 minutes. Preferably, the cooling sensation continues for the duration of the hot flash.

The compositions described herein may thus comprise a salt of a fatty acid, an alcohol, a sensate, water, and optional actives.

The compositions described herein may thus comprise a salt of a fatty acid, an alcohol, a sensate, water, and optional actives. The composition(s) may comprise a crystalline mesh. The crystalline mesh ("mesh") may comprise a relatively rigid, three-dimensional, interlocking crystalline skeleton frame of fiber-like crystalline particles (formed from a "crystallizing agent"), having voids or openings containing aqueous solution and optionally one or more actives. The compositions may be solid at 25° C. and 1 ATM. The mesh provides a self-supporting structure, such that a composition comprising such a mesh may 'stand on its own' when resting on a surface. If compressed above a critical stress, the mesh allows the composition to express the entrapped aqueous solution. A salt of a fatty acid may function as a "crystallizing agent" to form the crystalline mesh.

Salt of a Fatty Acid

The compositions described herein may comprise a salt of a fatty acid (or fatty acid salt). The compositions described herein may comprise 1% to about 12%, preferably from about 2% to about 10%, more preferably from about 4% to about 8%, by weight of a salt of a fatty acid. The fatty acid salts may be shorter chain-length fatty acid salts, where the carbon chain length is from about 13 to about 20, preferably from about 15 to about 18. The fatty acid salt may be a metal fatty acid salt, where the metal is preferably selected from the group consisting of sodium, potassium, magnesium, calcium, and lithium, more preferably sodium. The salt of a fatty acid may be selected from the group consisting of stearate, palmitate, myristate, tridecanoate, pentadecanoate, heptadecanoate, nanodecanoate, and mixtures thereof, preferably stearate, palmitate, myristate, and mixtures thereof. Preferably, the salt of a fatty acid is a metal fatty acid salt selected from the group consisting of sodium stearate, sodium palmitate, and sodium myristate.

Chain Length Blends

Select chain length blends allow the creation of effective mesh microstructures in compositions. The fatty acid salt may comprise a mixture of sodium carboxylate molecules, where each molecule has a specific chain length. For example, sodium stearate has a chain length of 18, sodium oleate has a chain length of 18:1 (where the 1 reflects a double bond in the chain), sodium palmitate has a chain length of 16, and so on. The chain length distribution—the quantitative weight fraction of each chain length in the fatty acid salt—can be determined by the BLEND TEST METHOD, as described below. Commercial sources of fatty acid salts usually comprise complicated mixtures of molecules, often with chain lengths between 10 to 22.

The compositions of the present disclosure have preferred chain length blends, as described by 'Optimal Purity' (Po) and 'Single Purity' (Ps), determined by the BLEND TEST METHOD. Sodium carboxylates can have an 'Optimal Chain Length' of between 13 to 22 carbons and can be used alone or combined to form mesh structures. Without wishing to be bound by theory, it is believed that sodium carboxylates having these select chain lengths (13 to 22) have a high solubilization temperature (e.g. Krafft Temperature) and can pack into crystals efficiently. Some sodium carboxylates have an 'Unsuitable Chain Length,' for example, 10, 12, 18:1 and 18:2 (and shorter or other unsaturated chain lengths). Compositions containing a sodium carboxylate having an 'unsuitable chain length,' alone or in combinations with an 'optimal chain length' molecule, do not form a desirable composition, e.g., a composition having a preferred stability temperature, firmness, and aqueous solution expression, as described below. Compositions comprising the preferred blends of fatty acid salts exhibit optimal stability temperature, firmness, and aqueous solution expression.

Po describes the total weight fraction of optimal chain length molecules of fatty acid salt to the total weight of fatty acid salt molecules, that is preferably Po>0.4, more preferably Po>0.6, more preferably Po>0.8 and most preferably Po>0.90. Ps describes the total weight fraction of the most common chain length molecule in the fatty acid salt to the total weight of fatty acid salt, that is preferably Ps>0.5, more preferably Ps>0.6, more preferably Ps>0.7, more preferably Ps>0.9.

The compositions described herein preferably comprise 'narrow blends'—or distributions of fatty acid chain lengths, more preferably blends that are substantially free of very short chain lengths (C12 or shorter) and/or measurable amounts of unsaturation on the carbon chains of the fatty acid salts. Single chain-length, saturated fatty acids having from about 13 to about 20 carbons are most preferred, particularly when coupled with a controlled crystallizing processing. Accordingly, the compositions described herein are best achieved when the blend of the chain length distribution is preferably greater than about Po>0.3, more preferably about Po>0.5, more preferably about Po>0.6, more preferably about Po>0.7 and most preferably about Po>0.8, as determined by the BLEND TEST METHOD. One skilled in the art, recognizes crystalline particles as exhibiting sharp scattering peaks between 0.25-60 deg. 2☐ in powdered x-ray diffraction measurements. This is in sharp contrast to compositions in which these materials are used as gelling agents, which show broad amorphic scattering peaks emanating from poorly formed solids which lack the long-range order of crystalline solids (FIG. 1).

Figure 2:
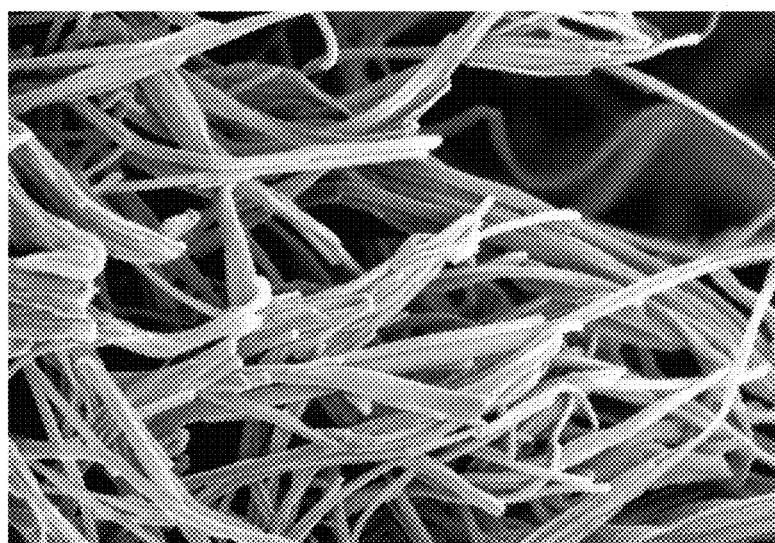
FIG. 2. SEM of crystalline mesh formed of fiber-like particles.

The fatty acid salt may function as a crystallizing agent and form the fiber-like crystalline particles that make up the mesh. The compositions described herein may comprise greater than about 80% water and be 'structured' by a mesh of interlocking, fiber-like crystalline particles of mostly single chain-length salts of fatty acids, as described above, see (FIG. 2). The term 'fiber-like crystalline particle' refers to a particle in which the length of the particle in the direction of its longest axis is greater than 10 times the length of the particle in any orthogonal direction. The fiber-like crystalline particles produce a mesh at very low concentrations (~0.5 wt %). The aqueous solution primarily resides in the open spaces of the mesh. In preparing these compositions, the fatty acid salt is dissolved in the aqueous solution using heat. The fiber-like crystalline particles form into the mesh as the mixture cools over minutes to hours.

Water

The compositions described herein may comprise water. The water may be distilled water, deionized water, or tap water. The compositions described herein may comprise about 70% to about 99.5%, preferably from about 75% to about 95%, or from about 75% to about 98%, more preferably about 80% to about 97%, even more preferably about 80% to about 92.5%, by weight of water.

Alcohols

The compositions described herein may comprise an alcohol, preferably a low molecular weight monohydric alcohol. The low molecular weight monohydric alcohol may be selected from the group consisting of methanol, ethanol, propanol, isopropanol, and mixtures thereof. The compositions described herein may comprise about from about 0.5% to about 15%, preferably from about 1% to about 10%, more preferably from about 2% to about 8%, by weight of an alcohol. Polyols, such as ethylene glycol and propylene glycol, may be included in the composition at low levels, for example, less than about 10%, less than about 5%, or less than about 1%. The composition may be substantially free of polyols, as polyols may leave a greasy or sticky residue on skin.

Sensates

The compositions described herein may comprise a sensate. The compositions described herein may comprise from about 0.1% to about 25%, preferably from about 0.25% to about 20%, more preferably from about 0.5% to about 15%, by weight of a sensate. Sensates provide a sensory benefit, such as a warming, tingling, or cooling sensation.

The sensate may be a cooling sensate (or coolant) that provides a physiological cooling effect, particularly on skin. Coolants are common ingredients in a wide variety of products, including compositions for topical application to the skin. The pleasant cooling sensation provided by coolants may contribute to the appeal and acceptability of products. In some instances, a coolant may provide an extended cooling sensation that lasts longer than the evaporative cooling provided by water and/or alcohol. In fact, compositions containing cooling sensates, when applied during a first hot flash event, may continue to provide a cooling sensation during a subsequent hot flash event, in effect delaying the subsequent hot flash and/or reducing the total number of hot flashes in a given time period. This may be particularly useful for treatment of night sweats, where the composition is applied by a user during a first hot flash event or prior to falling asleep, preventatively, and the composition continues to provide a cooling benefit during a subsequent hot flash event, when the user is asleep.

The manipulation of transient receptor potential ("TRP") channels has been described to create various sensations on skin. TRP receptors are also considered to include pain receptors. The general manipulation of TRP receptors is known. There are many different TRP receptors. Stimulation (by agonists) or blocking (by antagonists or by rapid desensitization) of specific TRPs and/or combinations thereof can provide sensate benefits. Sensations such as cool or cold can be attributed to stimulation, blocking or desensitization of receptors at peripheral nerve fibers by a stimulus, such as low temperature or a chemical coolant, which produces electrochemical signals that travel to the brain, which then interprets, organizes and integrates the incoming signal(s) into a perception or sensation. Different classes of receptors have been implicated in sensing cold temperatures or chemical coolant stimuli at mammalian sensory nerve fibers. Among these receptors, a major candidate involved in sensing cold has been identified and designated as cold- and menthol-sensitive receptor (CMR1) or TRPM8. TRPM8 activity is stimulated by stimuli including low temperatures, menthol, and other chemical coolants.

While it has been demonstrated that TRPM8 activity is stimulated by menthol and other coolants, it is not fully understood what other receptors may be involved and to what extent the activity of such receptors is stimulated or blocked in order to provide an overall perceived sensation that is pleasant, cooling, and refreshing. Menthol, for example, which is widely used as a cooling agent, can also produce other sensations including tingling, burning, prickling, and stinging. Menthol, therefore, may act on several different receptors, including cold, warm, pain and taste receptors. In particular, menthol is believed to activate the TRPA1 and TRPV1 receptors, which have been associated with the sensations of pain and irritation. It is believed that blocking the activity of the TRPA1 receptor and/or the TRPV1 receptor may provide skin irritation reduction benefits.

Ideally, a cooling sensate should produce a cooling or freshness sensation similar to that produced by menthol, but without the disadvantages associated with menthol, such as a strong odor and a burning or irritating sensation, particularly at high concentrations. Preferably, the cooling sensate stimulates the TRPM8 receptor, blocks or desensitizes the TRPA1 receptor, blocks or desensitizes the TRPV1 receptor, or a combination thereof. It is also desirable that the coolant compound barely possesses a distinctive odor while providing a pleasant, fresh cool sensation of prolonged duration, in order that the effect can still be perceived for a considerable time after use, for example, for more than 15 minutes. Menthol generally provides an initial high cooling impact, but its effect drops sharply within a few minutes after use. Some longer lasting coolant compounds, however, may not provide an immediate cooling perception, i.e., within a few seconds of application, particularly when used at low levels.

A number of coolant compounds of natural or synthetic origin are known. Coolants of natural origin include natural oil extracts. Natural oil extracts include peppermint oil, cornmint oil, spearmint oil, clove bud oil, eucalyptus oil, and mixtures thereof. Peppermint oil contains menthol, namely the (-)-menthol stereoisomer, which occurs most widely in nature and has the characteristic peppermint odor. There are eight stereoisomers of menthol (e.g., (-)-neomenthol, (-)-isomenthol, and (-)-neoisomenthol) and the different stereoisomers have different cooling potencies, with (-)-menthol providing the most potent cooling.

Among synthetic coolants, many are derivatives of or are structurally related to menthol, i.e., containing the cyclohexane moiety, and derivatized with functional groups including carboxamide, ketal, ester, ether and alcohol. Examples include ρ-menthanecarboxamides, such as N-ethyl-ρ-menthane-3-carboxamide (known commercially as WS-3), N-ethoxycarbonylmethyl-ρ-menthan-3-carboxamide (known commercially as WS-5), N-(4-methoxyphenyl)-ρ-menthan-3-carboxamide (known commercially as WS-12), N-tert-butyl-ρ-menthan-3-carboxamide (known commercially as WS-14), L-phenylephrine ρ-menthane carboxamide (CPS-195), N-(R)-2-oxotetrahydrofuran-3-yl-(1R,2S,5R)-ρ-menthane-3-carboxamide (D-HSL), N-benzo[1,3]dioxol-5-yl-3-ρ-menthanecarboxamide, N-benzooxazol-4-yl-3-ρ-menthanecarboxamide, N-Ethyl-2,2-diisopropylbutanamide)-ρ-menthane-3-carboxamide (known commercially as WS-27), (1R,2S,5R)-N-(4-(cyanomethyl)phenyl)menthylcarboxamide (Evercool™ 180 available from Givaudan), (1R,2S,5R)-N-(2-(pyridin-2-yl)ethyl)menthylcarboxamide (Evercool™ 190 available from Givaudan), (1R,2S,5R)-N-(4-(carbamoylmethyl)phenyl)-menthylcarboxamide, and mixtures thereof.

Carboxamides include 2-isopropyl-N,2,3-trimethyl-2-isopropylbutanamide (WS-23), N-(1,1-Dimethyl-2-hydroxyethyl)-2,2-diethylbutanamide (WS-116), N-(2-ethoxyethyl)-2-isopropyl-2,3-dimethylbutanamide, N-(2-Hydroxyethyl)-2,3-dimethyl-2-isopropylbutanamide, icilin (AG-3-5, 1-[2-hydroxyphenyl]-4-[2-nitrophenyl-]-1,2,3,6-tetrahydropyrimidine-2-one), N-(1-isopropyl-1,2- dimethylpropyl)-1,3-benzodioxole-5-carboxamide, 2-(p-tolyloxy)-N-(1H-pyrazol-5-yl)-N-((thiophen-2-yi)methyl) acetamide, N-Cyclopropyl-5-methyl-2-isopropylcyclohexanecarboxamide, and mixtures thereof.

Menthol derivatives include menthone, ormenthyl acetate, menthyl giutarate, menthyl methyl lactate, dimenthyl glutarate, 3-(1-menthoxy)propan-1-ol, 3-(1-menthoxy) butan-1-ol, menthyl nicotinate (NICOMENTHYL® available from Multichem R&D), isopulegol (COOLACT® P available from Vantage Specialty Ingredients), 3-(1-menthoxy)-2-methylpropane-1,2-diol, 3-(1-menthoxy)ethanol (COOLACT® 5 available from Vantage Specialty Ingredients), 3-((-)-menthoxy)propane-1,2-diol (COOLACT® 10 available from Vantage Specialty Ingredients), cis-p-menthane-3,8-diol & trans-p-menthane-3,8-diol (COOLACT® 38 available from Vantage Specialty Ingredients), menthyl pyrrolidin-2-one 5-carboxylate (QUESTICE® available from Givaudan), menthol ethylene glycol carbonate (Frescolat® MGC available from Symrise), menthol propylene glycol carbonate (FRESCOLAT® MFC available from Symrise), menthone glycerin acetal (FRESCOLAT® MGA available from Symrise), menthyl lactate (FRESCOLAT® ML available from Symrise), N,N-dimethyl menthyl succinamide, menthone (S)-lactic acid ketal (Freshone® available from Firmenich), (-)- Cubebol ((1R,4S,5R,6R,7S,10R)-7-isopropyl-4,10-dime 1-tricyclo[4.4.0.0(1,5)]decan-4-ol), menthyl acetoacetate (Ultracool 7), 3-(1-menthoxy)-propane-1,2-diol (TK-10, manufactured by Takasago), (1R,2S,5R)-2-[2-(2- isopropyl-5-methyl-cyclohexyloxy)ethoxy]-ethanol, (1R,4S,5R)-N-(2-ethoxyethyl)-2-isopropyl-5-methylcyclohexane-1-carboxamide, (1R,2R,4R)-1-(2-hydroxy-4-methylcyclohexyl)ethanone, menthyl ethylamido oxalate (FRESCOLANT® X-cool available from Symrise), and mixtures thereof.

Additional examples of cooling sensates include eucalyptol, borneol, 4-terpinol, camphor, methyl acetate, monomethyl succinate, dimethyl succinate, 2-(1 -methylpropyl)-cyclohexanone (FRESKOMENTHE® available from Givaudan), and a mixture of 2,2,5,6,6-pentamethyl-2,3,6,6a-tetrahydropentalen-3a(1H)-ol and 5-(2-hydroxy-2-methyl-propyl)-3,4,4-trimethylcyclopent-2-en-1-one.

Some sensates, including menthol itself and some natural oil extracts, may be less preferred because of their strong odor. Menthol derivatives and carboxamides may be preferred because these agents provide a cooling sensation comparable to that of menthol but without a strong odor. The compositions described herein may be substantially free of menthol.

Preferably, the sensate is a cooling sensate selected from the group consisting of menthol; 3-1-menthoxypropane-1,2-diol, menthyl lactate; N,2,3-trimethyl-2-isopropylbutanamide; N-ethyl-p-menthan-3-carboxamide; N-(4-cyanomethylphenyl)-ρ-menthanecarboxamide, and combinations thereof, more preferably, 3-1-menthoxypropane-1,2-diol, menthyl lactate; N,2,3-trimethyl-2-isopropylbutanamide; N-ethyl-p-menthan-3-carboxamide; N-(4-cyanomethylphenyl)-ρ-menthanecarboxamide, and combinations thereof.

The sensate may be dissolved in the water or dissolved with the low molecular weight monohydric alcohol (if present) in the water, where the sensate and the alcohol (if present) are comprised in the aqueous solution.

Additional Components

The compositions described herein may comprise additional components. The composition disclosed herein may comprise an additional component selected from the group consisting of a thickening agent, a preservative, a perfume (including but not limited to neat perfume oils, perfume microcapsules, and combinations thereof), an acid, a base, a salt, a chelant, a solvent, a surfactant, a polymer, a buffer, a colorant (including dyes, pigments, and combinations thereof), preferably selected from the group consisting of a thickening agent, a preservative, a perfume, and mixtures thereof, more preferably selected from the group consisting of a thickening agent, a perfume, and mixtures thereof.

Surfactant

Suitable surfactants include anionic surfactants, non-ionic surfactant, cationic detersive surfactants, zwitterionic surfactants and amphoteric surfactants and mixtures thereof. Suitable surfactants may be linear or branched, substituted or un-substituted, and may be derived from petrochemical material or biomaterial. When present, the total surfactant level is preferably from 0.1% to 60%, from 1% to 50% or even from 5% to 40% by weight of the subject composition.

Anionic surfactants include, but are not limited to, those surface-active compounds that contain an organic hydrophobic group containing generally 8 to 22 carbon atoms or generally 8 to 18 carbon atoms in their molecular structure and at least one water-solubilizing group preferably selected from sulfonate, sulfate, and carboxylate so as to form a water-soluble compound. Usually, the hydrophobic group will comprise a $C_8$-$C_{22}$ alkyl, or acyl group. Such surfactants may be employed in the form of water-soluble salts, where the salt-forming cation may be selected from sodium, potassium, ammonium, and magnesium, with the sodium cation being preferred.

Anionic surfactants may exist in an acid form, and the acid form may be neutralized to form a surfactant salt, which may be desirable for use in the disclosed compositions. Typical agents for neutralization include the metal counterion base such as hydroxides, e.g., NaOH or KOH. Further preferred agents for neutralizing anionic surfactants include ammonia, amines, oligamines, or alkanolamines. Suitable non-limiting examples including monoethanolamine, diethanolamine, triethanolamine, and other linear or branched alkanolamines known in the art; for example, highly preferred alkanolamines include 2-amino-1-propanol, 1-aminopropanol, monoisopropanolamine, or 1-amino-3-propanol. Amine neutralization may be done to a full or partial extent, e.g. part of the anionic surfactant mix may be neutralized with sodium or potassium and part of the anionic surfactant mix may be neutralized with amines or alkanolamines.

Suitable sulphonate surfactants include methyl ester sulphonates, alpha olefin sulphonates, alkyl benzene sulphonates, especially alkyl benzene sulphonates, preferably $C_{10}$-$_{13}$ alkyl benzene sulphonate. Alkyl benzene sulphonate (LAS) is typically made by sulphonating commercially available linear alkyl benzene (LAB). Suitable LAB includes low 2-phenyl LAB, such as those supplied by Sasol under the tradename Isochem® or those supplied by Petresa under the tradename Petrelab®, other suitable LAB include high 2-phenyl LAB, such as those supplied by Sasol under the tradename Hyblene®. A suitable anionic surfactant is alkyl benzene sulphonate that is obtained by DETAL catalyzed process, although other synthesis routes, such as HF, may also be suitable.

Suitable sulphate surfactants include alkyl sulphates, such as $C_{8\text{-}18}$ alkyl sulphate (e.g., $C_{12}$ alkyl sulphate) and alkyl alkoxylated sulphates, such as $C_{8\text{-}18}$ alkyl alkoxylated sulphates. Alkyl ethoxylated sulphates are preferred, such as $C_8$-$_{18}$ alkyl ethoxylated sulphates. The alkyl alkoxylated sulphate may have an average degree of alkoxylation of from 0.5 to 20, preferably from 0.5 to 10. $C_8$-$_{18}$ alkyl ethoxylated sulphates having an average degree of ethoxylation of from 0.5 to 10, or from 0.5 to 5, or from 0.5 to 3, are preferred. The alkyl alkoxylated sulfate may have a broad alkoxy distribution or a narrow/peaked alkoxy distribution.

The alkyl sulphates, alkyl alkoxylated sulphates, and alkyl benzene sulphonates may be linear or branched, e.g., 2-alkyl branched or mid-chain branched, substituted or un-substituted, and may be derived from petrochemical material or biomaterial. Preferably, the branching group is an alkyl. Typically, the alkyl is selected from methyl, ethyl, propyl, butyl, pentyl, cyclic alkyl groups, and mixtures thereof.

Alkyl sulfates and alkyl alkoxy sulfates are commercially available with a variety of chain lengths, degrees of alkoxylation, and degrees of branching. Commercially available sulfates include those derived from Neodol alcohols (Shell Company), Lial/Isalchem/Safol alcohols (Sasol company), or natural alcohols. Other suitable anionic detersive surfactants include alkyl ether carboxylates.

Suitable non-ionic detersive surfactants include $C_8$-$C_{18}$ alkyl ethoxylates, such as, NEODOL® non-ionic surfactants from Shell; $C_6$-$C_{12}$ alkyl phenol alkoxylates, where the alkoxylate units are preferably ethyleneoxy units, propyleneoxy units, or a mixture thereof $C_{12}$-$C_{18}$ alcohol and $C_6$-$C_{12}$ alkyl phenol condensates with ethylene oxide/propylene oxide block polymers such as Pluronic® from BASF; alkylpolysaccharides, preferably alkylpolyglycosides; methyl ester ethoxylates; polyhydroxy fatty acid amides; ether capped poly(oxyalkylated) alcohol surfactants; and mixtures thereof. The non-ionic surfactant may be selected from the group consisting of alkylpolyglucoside, alkyl alkoxylated alcohol, and combinations thereof.

Suitable alkyl alkoxylated alcohols include $C_8$-$_{18}$ alkyl alkoxylated alcohols. $C_8$-$_{18}$ alkyl ethoxylated alcohols are preferred. The alkyl alkoxylated alcohol may have an average degree of alkoxylation of from 1 to 50, or from 1 to 30, or from 1 to 20, or from 1 to 10. $C_8$-$_{18}$ alkyl ethoxylated alcohols having an average degree of ethoxylation of from 1 to 10, or from 1 to 7, or from 1 to 5, or from 3 to 7, are preferred. The alkyl alkoxylated alcohol can be linear or branched, substituted or un-substituted. Suitable nonionic surfactants include those with the trade name Lutensol® from BASF.

Suitable cationic detersive surfactants include alkyl pyridinium compounds, alkyl quaternary ammonium compounds, alkyl quaternary phosphonium compounds, alkyl ternary sulphonium compounds, and mixtures thereof. Preferred cationic detersive surfactants are quaternary ammonium compounds having the general formula:

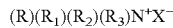

$(R)(R_1)(R_2)(R_3)N^+X^-$ where R is a linear or branched, substituted or unsubstituted $C_6$-$_{18}$ alkyl or alkenyl moiety, $R_1$ and $R_2$ are independently selected from methyl or ethyl moieties, $R_3$ is a hydroxyl, hydroxymethyl or a hydroxyethyl moiety, X is an anion which provides charge neutrality, preferred anions include: halides, preferably chloride; sulphate; and sulphonate.

Suitable amphoteric or zwitterionic detersive surfactants include amine oxides, and/or betaines. Preferred amine oxides are alkyl dimethyl amine oxide or alkyl amido propyl dimethyl amine oxide, more preferably alkyl dimethyl amine oxide and especially coco dimethyl amino oxide. Amine oxide may have a linear or mid-branched alkyl moiety. Typical linear amine oxides include water-soluble amine oxides containing one $R_1$ $C_8$-$_{18}$ alkyl moiety and 2 $R_2$ and $R_3$ moieties selected from the group consisting of $C_1$-$_3$ alkyl groups and $C_1$-$_3$ hydroxyalkyl groups. Preferably amine oxide is characterized by the formula $R_1$—N($R_2$)($R_3$) O, where $R_1$ is a $C_8$-$_{18}$ alkyl and $R_2$ and $R_3$ are selected from the group consisting of methyl, ethyl, propyl, isopropyl, 2-hydroxethyl, 2-hydroxypropyl and 3-hydroxypropyl. Linear amine oxide surfactants include linear C10-C18 alkyl dimethyl amine oxides and linear $C_8$-$C_{12}$ alkoxy ethyl dihydroxy ethyl amine oxides. Other suitable surfactants include betaines, such as alkyl betaines, alkylamidobetaine, amidazoliniumbetaine, sulfobetaine (INCI sultaines) as well as phosphobetaines.

Preservative

The compositions described herein may comprise a preservative. Preservatives are commonly used in such compositions to prevent or retard the formation of yeast, bacteria, and/or mold, thereby increasing the shelf life of the composition. Preservatives may be particularly beneficial for topical compositions that come in contact with skin and skin microbiota.

The composition of the present disclosure may comprise a preservative selected from the group consisting of benzoic acid and salts thereof, benzyl alcohol, benzylhemiformal, benzylparaben, 5-bromo-5-nitro-1,3-dioxane, 2-bromo-2-nitropropane-1,3-diol, butyl paraben, phenoxyethanol, methyl paraben, propyl paraben, diazolidinyl urea, sodium benzoate, calcium benzoate, calcium propionate, caprylyl glycol, biguanide derivatives, captan, chlorhexidine diacetate, chlorhexidine digluconate, chlorhexidine dihydrochloride, chloroacetamide, chlorobutanol, p-chloro-m-cresol, chlorophene, chlorothymol, chloroxylenol, m-cresol, o-cresol, DEDM hydantoin, DEDM hydantoin dilaurate, dehydroacetic acid, diazolidinyl urea, dibromopropamidine diisethionate, DMDM hydantoin, glyceryl caprylate, potassium sorbate, salicylic acid, hexamidine, caprytoyl glycine, 1,2-hexanediol, undecylenoyl glycine, ethylhexylglycerin, caprylhydroxamic acid, methylpropanediol, hinokitiol, sodium hinokitiol, phenylethyl alcohol, levulinec acid, p-anisic acid, 2-bromo-2-nitropi pane-1,3-diol, sodium hydroxymethylglycinate, iodopropynyl bulylcarbamatc, methylchloroisothiazolinone, methylisothiazolinone, piroclone olamine, cinnamon oil, rosemary extract, and combinations thereof.

Suitable levels of preservative are from about 0.0001 wt. % to about 0.5 wt. %, alternatively from about 0.0002 wt. % to about 0.2 wt. %, alternatively from about 0.0003 wt. % to about 0.1 wt. %, by weight of the composition.

Thickening Agents

The thickening agent may be provided in any amount known to one skilled in the art to facilitate achieving the desired viscosity in combination with the other ingredients in the composition. Thickening agents may be used to adjust the viscosity of a composition without substantially changing its other properties. Thickening agents may also improve the suspension of other ingredients. Some thickening agents may also function as stabilizers, when used to maintain the stability of an emulsion.

Non-limiting examples of thickeners that may be suitable for use herein include gums, modified gums, starches, modified starches, clays, and cross-linked water swellable polymers. The composition may comprise a thickening agent selected from the group consisting of carboxylic acid polymers, crosslinked polyacrylate polymers, polyacrylamide polymers, polysaccharides, gums, preferably xanthan gum, crosslinked vinyl ether/maleic anhydride copolymers, crosslinked poly(N-vinylpyrrolidones), and mixtures thereof, preferably selected from the group consisting of gums, preferably xanthan gum, carboxylic acid polymers, crosslinked polyacrylate polymers, polyacrylamide polymers, and mixtures thereof, more preferably selected from the group consisting of gums, preferably xanthan gum, crosslinked polyacrylate polymers, polyacrylamide polymers, and mixtures thereof. Xanthan gum is a preferred thickening agent.

The compositions may comprise from about 0.01% to about 10%, preferably from about 0.1% to about 5%, more preferably from about 0.2% to about 5% by weight of the composition, of a thickening agent.

Emollients

The disclosed compositions may comprise from about 0.001% to about 20%, preferably from about 0.01% to about 10%, more preferably from about 0.1% to about 5%, of the composition, of an emollient. Emollients tend to lubricate the skin, increase the smoothness and suppleness of the skin, prevent or relieve dryness of the skin, and/or protect the skin. Emollients may physically prevent or reduce moisture loss from the skin by formation of a water-impenetrable barrier over the stratum corneum. Emollients are typically water-immiscible, oily, or waxy materials. The level of emollient, when present, may vary according to the form of the composition.

Nonlimiting examples of emollients may include isopropyl isostearate, caprylic/capric triglycerides, petrolatum, dimethicone, dimethiconol, and mixtures thereof. The topical skincare composition may comprise an emollient selected from the group consisting of isopropyl isostearate, caprylic/capric triglycerides, petrolatum, dimethicone, dimethiconol, and mixtures thereof.

Vitamins

The composition disclosed herein may comprise a safe and effective amount of one or more vitamins. Nonlimiting examples of vitamins include vitamin B3 compounds, such as niacinamide, niacinnicotinic acid, tocopheryl nicotinate; vitamin B5 compounds, such as panthenol; vitamin A compounds and natural and/or synthetic analogs of Vitamin A, including retinoids, retinol, retinyl acetate, retinyl palmitate, retinoic acid, retinaldehyde, retinyl propionate, carotenoids (pro-vitamin A); vitamin E compounds, or tocopherol, including tocopheryl sorbate, tocopheryl acetate; vitamin C compounds, including ascorbate, ascorbyl esters of fatty acids, and ascorbic acid derivatives such as magnesium ascorbyl phosphate and sodium ascorbyl phosphate, ascorbyl glucoside, and ascorbyl sorbate, including derivatives of any of the aforementioned actives. The vitamin may be selected from the group consisting of xanthine compounds, vitamin B3 compounds, and panthenol compounds.

As used herein, "xanthine compound" means one or more xanthines, derivatives thereof, and mixtures thereof. Xanthine Compounds that can be useful herein include, but are not limited to, caffeine, xanthine, 1-methyl xanthine, theophylline, theobromine, derivatives thereof, and mixtures thereof. Among these compounds, caffeine is preferred in view of its solubility in the composition. The composition can contain from about 0.05%, preferably from about 2.0%, more preferably from about 0.1%, still more preferably from about 1.0%, and to about 0.2%, preferably to about 1.0%, more preferably to about 0.3% by weight of a xanthine compound As used herein, "vitamin B3 compound" means a compound having the formula:

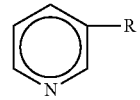

where R is —CONH$_2$ (i.e., niacinamide), —COOH (i.e., nicotinic acid) or —CH$_2$OH (i.e., nicotinyl alcohol); derivatives thereof; mixtures thereof; and salts of any of the foregoing. Exemplary derivatives of the foregoing vitamin B3 compounds include nicotinic acid esters, including non-vasodilating esters of nicotinic acid (e.g, tocopherol nicotinate, and myristyl nicotinate), nicotinyl amino acids, nicotinyl alcohol esters of carboxylic acids, nicotinic acid N-oxide and niacinamide N-oxide. The composition can contain from about 0.05%, preferably from about 2.0%, more preferably from about 0.1%, still more preferably from about 1.0%, and to about 0.1%, preferably to about 0.5%, more preferably to about 0.3% by weight of a vitamin B3 compound As used herein, the term "panthenol compound" is broad enough to include panthenol, one or more pantothenic acid derivatives, and mixtures thereof. panthenol and its derivatives can include D-panthenol ([R]-2,4-dihydroxy-N[3-hydroxypropyl)]-3,3-dimethylbutamide), DL-panthenol, pantothenic acids and their salts, preferably the calcium salt, panthenyl triacetate, royal jelly, panthetine, pantotheine, panthenyl ethyl ether, pangamic acid, pantoyl lactose, vitamin B complex, or mixtures thereof. The composition can contain from about 0.01%, preferably from about 0.02%, more preferably from about 0.05%, and to about 3%, preferably to about 1%, more preferably to about 0.5% 1w weight of a panthenol compound Salts The composition may comprise a salt, which can help with temperature stability. Non-limiting examples of salts can include sodium chloride, sodium sulfate, and combinations thereof. The composition may comprise from about 0.1 to about 10 wt. % of a salt, alternatively from about 1 to about 7 wt. %, alternatively 3 to about 5 wt. %, all by weight of the composition.

Sodium chloride (and other sodium salts) is a particularly useful additive to the aqueous solution to adjust the thermal stability of the composition. Not wishing to be bound by theory, sodium chloride is thought to 'salt out' the fatty acid salts, thereby decreasing the solubility of the fatty acid salts, which has the effect of increasing the thermal stability temperature of the composition, as measured by the THERMAL STABILITY TEST METHOD. For example, sodium chloride addition may increase the thermal stability temperatures of optimal chain length fatty acid salts by as much as 15° C. This may be particularly valuable, because the addition of other components into the aqueous solution often lowers the thermal stability temperature, in the absence of sodium chloride. However, adding sodium chloride can lead to adverse effects in the preparation of the compositions.

It is preferable in most making processes, to add sodium chloride into the hot fatty acid salt aqueous solution before cooling to form the mesh. However, adding too much may cause 'curding' of the fatty acid salts. The sodium chloride may also be added after the formation of the mesh, to provide the benefit of raising the thermal stability temperature at higher levels without curding. Finally, while the thermal stability temperature is increased with addition of sodium chloride, the addition of other non-sodium salts changes the fibrous nature of the crystals formed from the fatty acid salts, to form plates or platelet crystals, which are not desirable.

Solvents

The compositions may contain a solvent, separate from the alcohols described above. Non-limiting examples of solvents can include ethanol, glycerol, propylene glycol, polyethylene glycol 400, polyethylene glycol 200, and mixtures thereof. In one example the composition comprises from about 0.5% to about 15% solvent, in another example from about 1.0% to about 10% solvent, and in another example from about 1.0% to about 8.0% solvent, and in another example from about 1% solvent to about 5% solvent.

pH

The compositions of the present disclosure may be formulated to have a pH of about 10.5 or less. The compositions may have a pH ranging from about 2 to about 10.5, or about 3 to about 8, or from about 4 to about 7. The compositions may have a pH ranging from about 7 to about 10, preferably about 8.5 to about 10. pH may be measured at 80±2° C.

Firmness, Aqueous Solution Expression, and Thermal Stability

Surprisingly, it is possible to prepare the disclosed compositions to have sufficient firmness, aqueous solution expression, and thermal stability. Not wishing to be bound by theory, it is believed that sodium carboxylates present in high-water compositions (e.g. above about 80%) and correct chain length purity may form elongated, fiber-like crystal habits. These crystals form mesh structures even at very low concentrations. Firmness may be achieved by carefully adjusting the concentration and chain length distribution of the fatty acid salt. Aqueous solution expression may be achieved by compression above a yield behavior that breaks the mesh structure, allowing the water to flow from the composition. One skilled in the art recognizes this as a plastic deformation of the mesh structure. This stands in contrast to other gelling agents like gelatin, that can be formulated at very high-water concentrations but do not express water with compression. Thermal Stability may be achieved by ensuring the proper chain length and chain length distributions to ensure the mesh does not solubilize when heated above 40° C. This is an important property in relation to the shelf-life and supply chain for consumer products. Addition of sodium chloride can be used to increase the thermal stability of the composition. Also, the disclosed compositions are prepared by cooling the mixture largely quiescently, in contrast to a freezer or other mechanically invasive processes. Not wishing to be bound by theory, quiescent processes allow the formation of very large and efficient fibrous crystals rather the breaking them into smaller less efficient crystals.

Aqueous Solution Expression

Aqueous solution is expressed in work to express water per unit volume, where preferred compositions are between 300 J m-3 and about 9,000 J m-3, more preferably between 1,000 J m-3 and about 8,000 J m-3, more preferably between 2,000 J m-3 and about 7,000 J m-3 and most preferably between 2,500 J m-3 and about 6,000 J m-3, as determined by the AQUEOUS SOLUTION EXPRESSION TEST METHOD. These limits allow for viable product compositions that—for example, provide evaporative and/or sensate-based cooling when the composition is applied to the skin and cleaning when applied to a hard surface. These work limits are in contrast to bar soaps and deodorant sticks that do not express aqueous solution when compressed. These work limits are also in contrast to gelatins that likewise do not express water when compressed. So, it is surprising that high-water compositions can be created with these materials, that express aqueous solution with compression. Not wishing to be bound by theory, it is believed this a result of a network of crystalline materials that break up during the application of sufficient stress—releasing the aqueous solution with no uptake when the compression is released.

Firmness

The preferred firmness of the compositions disclosed herein is between about 0.5 N to about 25.0 N, more preferably between 1.0 N to about 20.0 N, more preferably between 3.0 N to about 15.0 N and most preferably between 5.0 N and about 10.0 N. These firmness values allow for viable product compositions that may retain their shape when resting on a surface, and as such are useful as a rheological solid stick to provide a dry-to-the-touch but wet-to-the-push properties. The firmness values are significantly softer than bar soaps and deodorants, which exceed these values. So, it is surprising that high-water compositions can be created that remain as solid compositions with between about 0.25 wt % to about 10 wt % fatty acid salt, more preferably between about 0.5 wt % to about 7 wt % fatty acid salt and most preferably between about 1 wt % to about 5 wt % fatty acid salt. Not wishing to be bound by theory, it is believed this a result of fatty acid salts creating the interlocking mesh that provides sufficient firmness.

Thermal Stability

Thermal stability is used to ensure that the disclosed compositions can be delivered as intended to the consumer through the supply chain, preferably with thermal stability greater than about 40° C., more preferably greater than about 45° C., and most preferably greater than about 50° C., as determined by the THERMAL STABILITY TEST METHOD. Creating compositions with acceptable thermal stability is difficult, as it may vary unpredictably with concentration of the fatty acid salt and other component(s). Not wishing to be bound by theory, thermal stability results from the insolubility of the fatty acid salt in the aqueous solution. Conversely, thermal instability is thought to result from complete solubilization of the fatty acid salt that comprised the mesh.

Methods of Use

The compositions of the present disclosure may be used to treat keratinous tissue. The treatment method may include the steps of providing a composition according to the present disclosure and applying a safe and effective amount of the composition to at least a portion of a user's keratinous tissue, where the keratinous tissue is skin or hair, and optionally leaving the composition on the keratinous tissue for at least about sixty seconds, or at least about 5 minutes, or at least about 30 minutes, or at least about 60 minutes, preferably for at least several hours, or until the next application of the topical composition. The composition need not be rinsed and does not leave a sticky residue. Also, the application of the composition does not interfere with the application of other treatment compositions, such as moisturizer or makeup.

The compositions of the present disclosure may be used to treat hot flashes. The treatment method may include the steps of providing to a user in need thereof a composition comprising from about 0.01% to about 10%, preferably from about 1% to about 9%, more preferably from about 2% to about 8%, by weight of a salt of a fatty acid containing from about 13 to about 20 carbon atoms, from about 70% to about 99.5%, preferably from about 75% to about 98%, more preferably from about 80% to about 97%, by weight water; applying a safe and effective amount of the composition to at least a portion of keratinous tissue of the user, where the keratinous tissue is skin or hair; and optionally leaving the composition on the keratinous tissue for at least about sixty seconds, or at least about five minutes, or at least about thirty minutes, or at least about one hour, preferably for at least several hours, or until the next application of the topical composition. The composition may further comprise from 0.5% to about 15%, preferably from about 1% to about 10%, more preferably from about 2% to about 8%, by weight of an alcohol selected from the group consisting of methanol, ethanol, propanol, isopropanol, and mixtures thereof, and from about 0.1% to about 25%, preferably from about 0.25% to about 20%, more preferably from about 0.5% to about 15%, by weight of a sensate.

The keratinous tissue may be on one of the following body parts: the lips, the face, the forehead, the neck, the arm, preferably the underarm, the upper and/or forearm, or a combination thereof, the wrist, the hands, the chest, the back, the loin, the leg, the thigh, the abdomen, or a combination thereof. For more discrete use, the composition may be applied to keratinous tissue that is not covered by clothing, such as the face, forehead, neck, wrist, hands, forearm, or combinations thereof.

A safe and effective amount of the composition may be from about 0.1 g to about 5 g, preferably from about 0.2 g to about 4 g, more preferably about 0.3 g to about 3 g of the composition per day. The composition may be used one or more times a day. From about 0.1 g to about 2 g, preferably from about 0.2 g to about 1 g, more preferably from about 0.3 g to about 0.8 g of the composition may be applied per use. For example, 0.39 g may be applied per use, six times a day, for a total of 2.34 g per day.

The disclosed compositions, when applied during a first hot flash event, may continue to provide a cooling benefit during a subsequent hot flash event. This may be particularly useful for treatment of night sweats, where the composition is applied by a user during a first hot flash event or prior to falling asleep and the composition continues to provide a cooling benefit during a subsequent hot flash event, when the user is asleep.

The compositions described herein may provide, upon use, an immediate onset of a cooling sensation and the cooling sensation may extend for about 10 second to about 60 minutes, or from about 10 seconds to about 30 minutes, or from about 10 seconds to about 20 minutes, or from about 10 seconds to about 15 minutes. The average hot flash lasts from about 30 seconds to about 10 minutes. Preferably, the cooling sensation continues for the duration of the hot flash.

The disclosed compositions may be provided in a package depending upon the product form, such as for example, in a jar, in a squeeze tube, in a bottle, in a canister, or any such package known to one skilled in the art to deliver topical compositions. The product may take the form of a stick, a cylinder, a button, or a sphere in a single container. The product may be packaged in an elevator/threaded spindle dispensing package. Such packages typically have a tubular body or barrel and a threaded spindle, which is connected to a hand wheel on the exterior of the package, at the bottom of the package. Turning the hand wheel in a particular direction advances the elevator towards the top of the package, thereby dispensing the composition, while turning the hand wheel in the opposite direction retracts it back towards the bottom.

TEST METHODS pH Test Method

Unless otherwise stated herein, the pH of the composition is defined as the pH of the composition at 80±2° C. pH can be measured using a standard pH meter such as, for example, a Beckman Coulter model PHI1410 pH meter equipped with a general-purpose probe (manufactured by Beckman Coulter, Brea, Calif., U.S.A.). The pH meter is calibrated according to the manufacturer's instructions.

Firmness Test Method

All samples and procedures are maintained at room temperature (25±3° C.) prior to and during testing, with care to ensure little or no water loss.

All measurements were made with a TA-XT2 Texture Analyzer (Texture Technology Corporation, Scarsdale, N.Y., U.S.A.) outfitted with a standard 45° angle penetration cone tool (Texture Technology Corp., as part number TA-15).

To operate the TA-XT2 Texture Analyzer, the tool is attached to the probe carrier arm and cleaned with a low-lint wipe. The sample is positioned and held firmly such that the tool will contact a representative region of the sample. The tool is reset to be about 1 cm above the product sample.

The sample is re-positioned so that the tool will contact a second representative region of the sample. A run is done by moving the tool at a rate of 2 mm/second exactly 10 mm into the sample. The "RUN" button on the Texture Analyzer can be pressed to perform the measurement. A second run is done with the same procedure at another representative region of the sample at sufficient distance from previous measurements that they do not affect the second run. A third run is done with the same procedure at another representative region of the sample at sufficient distance from previous measurements that they do not affect the third run.

The results of the FIRMNESS TEST METHOD are all entered in the examples in the row entitled 'Firmness.' In general, the numeric value returned is the average of the maximum value of the three measurements as described above, except in one of the two cases: 1) the composition does not form a homogenous rheological solid (e.g. completely or partially liquid), the value of 'NM1' is returned; 2) and, the composition curds during making, the value of 'NM2' is returned.

Thermal Stability Test Method

All samples and procedures are maintained at room temperature (25±3° C.) prior to testing.

Sampling is done at a representative region on the sample, in two steps. First, a spatula is cleaned with a laboratory wipe and a small amount of the sample is removed and discarded from the top of the sample at the region, to create a small square hole about 5 mm deep. Second, the spatula is cleaned again with a clean laboratory wipe, and a small amount of sample is collected from the square hole and loaded into DSC pan.

The sample is loaded into a DSC pan. All measurements are done in a high-volume-stainless-steel pan set (TA part #900825.902). The pan, lid and gasket are weighed and tared on a Mettler Toledo MT5 analytical microbalance (or equivalent). The sample is loaded into the pan with a target weight of 20 mg (+/−10 mg) in accordance with manufacturer's specifications, taking care to ensure that the sample is in contact with the bottom of the pan. The pan is then sealed with a TA High Volume Die Set (TA part #901608.905). The final assembly is measured to obtain the sample weight.

The sample is loaded into TA Q Series DSC in accordance with the manufacture instructions. The DSC procedure uses the following settings: 1) equilibrate at 25° C.; 2) mark end of cycle 1; 3) ramp 1.00° C./min to 90.00° C.; 4) mark end of cycle 3; then 5) end of method; Hit run.

The results of the TEMPERATURE STABILITY TEST METHOD are all entered in the examples in the row entitled 'Temperature.' In general, the numeric value is returned as described above, except in one of the two cases: 1) the composition does not form a homogenous rheological solid (e.g. completely or partially liquid) and is not suitable for the measurement, the value of 'NM3' is returned; and 2) the composition curds during making and is not suitable for the measurement, the value of 'NM4' is returned.

Aqueous Solution Expression Test Method

All samples and procedures are maintained at room temperature (25±3° C.) prior to testing.

Measurements for the determination of aqueous solution express are made with a TA Discovery HR-2 Hybrid Rheometer (TA Instruments, New Castle, Del., U.S.A.) and accompanying TRIOS software version 3.2.0.3877, or equivalent. The instrument is outfitted with a DHR Immobilization Cell (TA Instrument) and 55 mm flat steel plate (TA Instruments). The calibration is done in accordance with manufacturer's recommendations, with special attention to measuring the bottom of the DHR Immobilization Cell, to ensure this is established as gap=0.

Samples are prepared in accordance with EXAMPLE procedures. A sample is prepared in a Speed Mixer container (Flak-Tech, Max 60 Cup Translucent, Cat #501 222t), so that the diameter of the sample matches the diameter of the HR-2 Immobilization Cell. The sample is released from the container by running a thin spatula between the edge of the container and the sample. The container is gently turned over and placed on a flat surface. A gentle force is applied to the center of the bottom of the overturned container, until the sample releases and gently glides out of the container. The sample is carefully placed in the center ring of the DHR Immobilization Cell. Care is used to ensure that the sample is not deformed and re-shaped through this entire process. The diameter of the sample should be slightly smaller than the inner diameter of the ring. This ensures that force applied to the sample in latter steps does not significantly deform the cylindrical shape of the sample, instead allowing the fluid to escape through the bottom of the sample. This also ensures that any change in the height of the sample for the experiment is equivalent to the amount of aqueous solution expressed during the test. At the end of the measurement, one should confirm that the aqueous solution is indeed expressed from the sample through the measurement, by looking for water in the effluent tube connected to the Immobilization Cell. If no aqueous solution is observed, the sample is deemed not to express water.

Instrument settings are set as follows. Select Axial Test Geometry. Then, set "Geometry" options: Diameter=50 mm; Gap=45000 um; Loading Gap=45000 um; Trim Gap Offset=50 um; Material='Steer'; Environmental System="Peltier Plate". Set "Procedure" options: Temperature=25° C.; Soak Time=0 sec; Duration=2000 sec; Motor Direction="Compression"; Constant Linear Rate=2 um sec-1; Maximum Gap Change=0 um; Torque=0 uN·m; Data Acquisition='save image' every 5 sec.

The steel tool is manually moved within about 1000 um of the surface of the sample, taking care that the tool does not touch the surface. In the "Geometry" options, reset Gap to this distance.

The run is then started.

The data is expressed in two plots: 1) Plot 1: Axial Force (N) on the left-y-axis and Step Time (s) on the x-axis; 2) Plot 2: Gap (um) on the right-y-axis and Step Time (s) on the x-axis.

The Contact Time—T(contact), is obtained from Plot 1. The T(contact) is defined as the time when the tool touches the top of the sample. The T(contact) is the Step Time when the first Axial Force data point exceeds 0.05 N.

The Sample Thickness—L, is the gap distance at the Contact Time, and expressed in units of meters.

The Time of Compression—T(compression), is the Step Time at which the gap is 0.85*L, or 15% of the sample.

The Work required to squeeze the water from the structure is the area under the Axial Force curve in Plot 1 between T(contact) and T(compression) multiplied by Constant Linear Rate, or 2e-6 m s-1 normalized by dividing the total volume of expressed fluids, and is expressed in units of Joules per cubic meter (J m-3).

The results of the AQUEOUS SOLUTION EXPRESSION TEST METHOD, are all entered in the examples in the row entitled 'AP Expression.' In general, the numeric value, as the average of at least two replicates, is returned as described, except in one of the three cases: 1) the composition does not form a homogenous rheological solid (e.g. completely or partially liquid) and is not suitable for the measurement, the value of 'NM5' is returned; 2) the composition curds during making and is not suitable for the measurement, the value of 'NM6' is returned; 3) the composition is a rheological solid but too soft to effectively load in the device, the value of 'NM7' is returned; and 4) the composition is too hard so that the force exceeds 50 N before the 15% compression, the value of 'NM8' is returned.

Blend Test Method

All samples and procedures are maintained at room temperature 25 (±3° C.) prior to testing.

Samples are prepared by weighing 4 mg (+/−1 mg) of a 3% fatty acid in water solution into a scintillation vial with a PTFE septum and then adding 2 mL of ethanol ACS grade or equivalent. A cap is then placed on the vial and the sample is mixed until the sample is homogenous. The vial is then placed in a 70° C. oven with the cap removed to evaporate the ethanol (and water), after which it is allowed to cool to room temperature.

A pipettor is used to dispense 2 mL of BF3-methanol (10% Boron Trifluoride in methanol, Sigma Aldrich #15716) into the vial, and the capped tightly. The sample is placed on a VWR hot plate set at 70° C. until the sample is homogenous, and then for an additional 5 min before cooling to room temperature.

A saturated sodium chloride solution is prepared by adding sodium chloride salt ACS grade or equivalent to 10 mL of distilled water at ambient temperature. Once the vial is at room temperature, 4 mL of the saturated sodium chloride solution are added to the vial and swirled to mix. Then, 4 mL of hexane, ACS grade or equivalent, are added to the vial which is then capped and shaken vigorously. The sample is then placed on a stationary lab bench and until the hexane and water separate into two phases.

A transfer pipet is used to transfer the hexane layer into a new 8 mL vial, and then 0.5 g of sodium sulfate, ACS grade or equivalent, is added to dry the hexane layer. The dried hexane layer is then transferred to a 1.8 mL GC vial for analysis.

Samples are analyzed using an Agilent 7890B (Agilent Technologies Inc., Santa Carla, Calif.), or equivalent gas chromatograph, equipped with capillary inlet system and flame ionization detector with peak integration capabilities, and an Agilent DB-FastFAME (#G3903-63011), or equivalent column.

The gas chromatograph conditions and settings are defined as follows: uses Helium UHP grade, or regular grade helium purified through gas purification system, as a carrier gas, and is set at a constant flow mode of 1.2 mL/minute (velocity of 31.8 cm/sec); has an oven temperature program that is set for 100° C. for 2 minutes, and increased at a rate of 10° C. per minute until it reaches 250° C. for 3 minutes; the injector temperature is set to 250° C. and the detector temperature is set to 280° C.; the gas flows are set to 40 mL/minute for hydrogen, 400 mL/minute for air, and 25 mL/minute for the Make-up (helium); and the injection volume and split ratio is defined a 1 uL, split 1:100 injection.

The instrument is calibrated using a 37-Component FAME standard mixture (Supelco #CRM47885), or equivalent calibration standard. The Response Factor and Normalized Response Factor based on n-C16 FAME standard.

Response Factor is calculated for each component by dividing the FAME FID Area account of an analyte in the calibration solution by the concentration of the identical FAME analyte in the calibration solution.

The Normalized Response Factor is calculated by dividing the Response Factor of each component by the Response Factor of n-C16 methyl ester that has been defined as 1.00.

The Normalized FAME FID Area is calculated with the Normalized Response Factor by dividing the FAME FID area (component) by the Normalized Response Factor (component).

The FAME weight percent of each component is calculated by dividing the Normalized FAME FID area (component) by the Normalized FAME FID area (total of each component) and then multiplying by one hundred.

The Conversion Factor from FAME to free Fatty Acid is calculated by dividing the Molecular Weight of the Target Fatty Acid by the Molecular Weight of the Target FAME.

The Normalized Fatty Acid FID Area is calculated by multiplying the Normalized FAME FID Area by the Conversion Factor from FAME to free Fatty Acid.

The Fatty Acid Weight Percent of each component is calculated by dividing the Normalized Fatty Acid FID Area (component) by the Normalized FA FID Area (total of each component) and the multiplying the result by one hundred.

The Conversion Factor from FAME to free Fatty Acid Sodium Salt is calculated by dividing the Molecular Weight of the Target Fatty Acid Sodium Salt by the molecular weight of the Target FAME.

The Normalized Fatty Acid Sodium Salt FID Area is calculated by multiplying the Normalized FAME FID Area by the Conversion Factor from FAME to free Fatty Acid Sodium Salt.

The Weight percent of each Fatty Acid Sodium Salt component was calculated by dividing the normalized Fatty Acid Sodium Salt FID area (component) by the Normalized Fatty Acid Sodium Salt FID area (total of each component) and then multiplying by one hundred.

Purity of the fatty acid salt is described in the following ways: Optimal Purity—Po, which is the mass fraction of the optimal chain length molecules in the fatty acid salt blend calculated as:

$$Po = \frac{\sum Mo}{Mt}$$

where Mo is the mass of each optimal chain length in the fatty acid salt and Mt is the total mass of the fatty acid salt. Single Purity—Ps, which is the mass fraction of the most common chain length in the fatty acid salt blend calculated as:

$$Ps = \frac{Ms}{Mt}$$

where Ms is the mass of the most common chain length in the fatty acid salt and Mt is the total mass of the fatty acid salt. The value is expressed in brackets—[Ms], if the most common chain length is selected from the group of unsuitable chain length molecules.

EXAMPLES

Examples 1 Through 8

Compositions in Table 1 are prepared using a heated mixing device. An overhead mixer (IKA Works Inc, Wilmington, NC, model RW20 DMZ) and a three-blade impeller design is assembled. All preparations are heated on a heating-pad assembly (VWR, Radnor, PA, 7×7 CER Hotplate, cat. no. NO97042-690), where heating is controlled with an accompanying probe.

The solutions are prepared by adding water and sodium myristate to a stainless-steel beaker (Thermo Fischer Scientific, Waltham, MA). The beaker is placed on the heated mixing device. The overhead stirrer is placed in the beaker and set to rotate at 100 rpm. The heater is set to 80° C. The preparation is heated to 80° C. The solution is then cooled down to 60° C., at which time the L-menthol, ethanol, and FRESCOLAT® MGA are added and mixed until thoroughly dissolved. Sodium chloride is added and further mixed until thoroughly dissolved. The solution is then divided into three 60 g plastic jars (Flak-Tech, Max 60 Cup Translucent, Cat #501 222t): one jar is filled to 50 ml and two jars are filled to 25 ml. The samples are cooled at room temperature 25° C. (±3° C.) until solid. Firmness measurements are made on the 50 ml samples with the FIRMNESS TEST METHOD and a thermal stability measurements are made by the THERMAL STABILITY TEST METHOD on the 50 ml samples. Water-expression measurements are made by the WATER-EXPRESSION TEST METHOD on the two 25 ml samples. A value of 'NM' in Table 1 means that a composition is pre-screened by placing the composition in an oven set at 40° C. for 60 minutes, and the composition is not tested further if the resulting sample is completely or partially liquid.

TABLE 1

|  | Ex. 1 | Ex. 2 | Ex. 3 | Ex. 4 | Ex. 5 | Ex. 6 | Ex. 7 | Ex. 8 |
|---|---|---|---|---|---|---|---|---|
| Water[1] | 90.6% | 88.6% | 86.6% | 84.6% | 89.5% | 89.1% | 88.1% | 82.6% |
| NaM[2] | 4.0% | 6.0% | 8.0% | 10.0% | 6.0% | 6.0% | 6.0% | 6.0% |
| Ethanol[3] | 4.0% | 4.0% | 4.0% | 4.0% | 4.0% | 4.0% | 4.0% | 4.0% |
| L-Menthol[4] | 0.2% | 0.2% | 0.2% | 0.2% | 0.1% | 0.2% | 0.2% | 0.2% |
| MGA[5] | 1.1% | 1.1% | 1.1% | 1.1% | 0.4% | 0.8% | 0.8% | 1.1% |
| NaCl[6] | 0.0% | 0.0% | 0.0% | 0.0% | 0.0% | 0.0% | 1.0% | 6.0% |
| Firmness | 1.8N | 10.0N | 24.8N | 31.5N | 21.2N | 16.1N | 13.7N | 12.9N |
| Water Expression | NM | NM | 526 J m−3 | 3,390 J m−3 | 4,670 J m−3 | NM | 1,520 J m−3 | — |
| Temperature | NM | NM | 36.6° C. | 40.0° C. | 36.4° C. | NM | 43.9° C. | 58.2° C. |
| Purity – Po | 1.0 | 1.0 | 1.0 | 1.0 | 1.0 | 1.0 | 1.0 | 1.0 |
| Purity – Ps | 1.0 | 1.0 | 1.0 | 1.0 | 1.0 | 1.0 | 1.0 | 1.0 |

[1]Water: Millipore, Burlington, MA (18 m-ohm resistance)
[2]Sodium myristate (sodium tetradecanoate, NaC14): TCI Chemicals, Cat. # M0483
[3]Ethanol (200 proof)
[4]L-Menthol - Sigma-Aldrich
[5]FRESCOLAT ® MGA: Symrise
[6]Sodium chloride

Examples 9 Through 18

The compositions in Table 2 are prepared using a heated mixing device. An overhead mixer (IKA Eurostar 40 Digital Overhead Mixer, Model #EURO-ST 40 D S001) and a 4-blade flat impeller is used. All preparations are heated on a hot plate (IKA C-Mag HS 7 Hot Plate; Model #C-MAG HS 7 S1), where the composition temperature is controlled with an accompanying probe (IKA ETS-D5 Temperature Probe; Model #ETS-D5).

The samples are prepared by adding water to a stainless-steel beaker. An overhead mixer is inserted into the water and started at a speed sufficient to induce vortex motion, while allowing the temperature to heat to 85° C. Xanthan gum is then slowly added and, when the solution is free of clumps, sodium chloride is added and stirred into solution. Ethanol followed by sodium myristate or sodium palmitate is then added. Separately, the pentaerythrityl tetraisostearate and cooling sensate (L-menthol, FRESCOLAT® MGA, and WS-5) are added to a 20 ml glass vial. This vial is placed in an 85° C. water bath and periodically manually swirled until a homogenous mix is created. Once the sodium myristate or sodium palmitate is dissolved into solution and the mix in the stainless-steel beaker reaches 80° C., the contents of the 20 ml vial are poured into the beaker, followed by perfume. The speed of mixer is increased to compensate, if needed, to continue the vortex motion. Mixing continues for five minutes, then the resulting mix is dispensed into molds and allowed to cool at room temperature.

TABLE 2

|  | Ex. 9 | Ex. 10 | Ex. 11 | Ex. 12 | Ex. 13 | Ex. 14 | Ex. 15 | Ex. 16 | Ex. 17 | Ex. 18 |
|---|---|---|---|---|---|---|---|---|---|---|
| NaM[1] | 0.0% | 0.0% | 0.0% | 0.0% | 0.0% | 0.0% | 0.0% | 0.0% | 0.0% | 4.8% |
| NaP[2] | 5.0% | 5.0% | 5.0% | 5.0% | 5.0% | 5.0% | 5.0% | 5.0% | 4.8% | 0.0% |
| Water[3] | 73.6% | 73.5% | 73.5% | 73.5% | 74.1% | 74.1% | 74.1% | 74.1% | 77.2% | 77.2% |
| NaCL[4] | 3.5% | 3.5% | 3.5% | 3.5% | 3.5% | 3.5% | 3.5% | 3.5% | 3.4% | 3.4% |
| Xanthan Gum[5] | 0.3% | 0.3% | 0.3% | 0.3% | 0.3% | 0.3% | 0.3% | 0.3% | 0.3% | 0.3% |
| EtOH[6] | 5.0% | 5.1% | 5.0% | 5.0% | 5.0% | 5.0% | 5.0% | 5.0% | 7.8% | 7.9% |
| L Menthol[7] | 8.0% | 0.0% | 0.0% | 0.0% | 8.0% | 0.0% | 0.0% | 0.0% | 0.0% | 0.0% |
| MGA[8] | 0.0% | 8.0% | 0.0% | 0.0% | 0.0% | 8.0% | 0.0% | 0.0% | 3.9% | 3.9% |
| WS-5[9] | 0.0% | 0.0% | 0.0% | 8.0% | 0.0% | 0.0% | 0.0% | 8.0% | 0.0% | 0.0% |
| ML Nat[10] | 0.0% | 0.0% | 8.1% | 0.0% | 0.0% | 0.0% | 8.0% | 0.0% | 0.0% | 0.0% |
| Perfume | 0.5% | 0.5% | 0.5% | 0.5% | 0.0% | 0.0% | 0.0% | 0.0% | 0.5% | 0.5% |
| PhEtOH[11] | 0.0% | 0.0% | 0.0% | 0.0% | 0.0% | 0.0% | 0.0% | 0.0% | 0.0% | 0.0% |
| C'Ester PTIS[12] | 4.0% | 4.0% | 4.1% | 4.1% | 4.0% | 4.0% | 4.0% | 4.0% | 2.0% | 2.0% |

[1]Sodium myristate (sodium tetradecanoate, NaC14): TCI Chemicals, Cat. # M0483 - AKA TCI NaM
[2]Sodium palmitate (sodium hexadecanoate, NaC16): TCI Chemicals, Cat. # P0007 - AKA TCI NaP
[3]Water: Millipore, Burlington, MA (18 m-ohm resistance)
[4]Sodium chloride
[5]Xanthan Gum: CP Kelco
[6]Ethanol (200 proof)
[7]L-Menthol - Sigma-Aldrich
[8]FRESCOLAT ® MGA: Symrise
[9]WINSENSE ™ WS-5: Symrise
[10]FRESCOLAT ® ML Nat.: Symrise
[11]PROTECTOL ® PE: 2-phenoxyethanol sold by BASF
[12]Pentaerythrityl tetraisostearate: Custom Synthesis, LLC

Examples 19 Through 48

The examples in Table 3, 4, and 5 are heated in a heat block (IKA Dry Block Heater 3; Model #DBH 3 S001) and stirred on a stir plate (VWR Standard Multiposition Stirrer; Model #: 12621-042).

The examples are prepared by adding heated (~80° C.) water to a 20 mL glass scintillation vial with a small stirrer bar. The sodium chloride is then added and the vial is capped and placed into the heater block set for 80° C. Once the salt is dissolved into solution, sodium myristate, sodium palmitate, or sodium stearate is added. Occasionally the vial is removed from the heater block and placed on a stir plate that is set so that vortex mixing occurrs. After approximately three to five minutes of mixing, the vial is returned to the heater block. The cycling of placing the vial in the heater block and then onto the stir plate is repeated until the sodium myristate, sodium palmitate, or sodium stearate is dissolved into solution. Once the sodium myristate, sodium palmitate, or sodium stearate is dissolved, ethanol, a cooling sensate (FRESCOLAT® MGA and WS-5), phenoxyethanol, petrolatum, and perfume is added to the vial. The vial is allowed to stir on the stir plate for approximately one to two minutes before being placed back into the heater block. The vial is then occasionally removed from the heater block and placed onto the stir plate, until all contents are dissolved. The resulting mix is dispensed into molds and allowed to cool at room temperature.

TABLE 3

|  | Ex. 19 | Ex. 20 | Ex. 21 | Ex. 22 | Ex. 23 | Ex. 24 | Ex. 25 | Ex. 26 | Ex. 27 | Ex. 28 |
| --- | --- | --- | --- | --- | --- | --- | --- | --- | --- | --- |
| NaM[1] | 6.0% | 6.1% | 6.1% | 5.7% | 7.4% | 8.0% | 3.7% | 6.2% | 5.9% | 6.1% |
| Water[2] | 87.3% | 89.4% | 85.3% | 86.7% | 84.7% | 82.5% | 91.1% | 87.3% | 81.3% | 84.2% |
| NaCL[3] | 2.2% | 0.0% | 3.0% | 3.0% | 2.9% | 4.9% | 0.0% | 0.0% | 3.1% | 0.0% |
| EtOH[4] | 0.0% | 0.0% | 0.0% | 0.0% | 0.0% | 0.0% | 4.9% | 4.5% | 5.1% | 5.1% |
| MGA[5] | 4.2% | 4.2% | 5.2% | 4.1% | 4.4% | 4.1% | 0.0% | 1.6% | 4.3% | 4.2% |
| WS-5[6] | 0.0% | 0.0% | 0.0% | 0.0% | 0.0% | 0.0% | 0.0% | 0.0% | 0.0% | 0.0% |
| Perfume | 0.0% | 0.0% | 0.0% | 0.1% | 0.1% | 0.1% | 0.0% | 0.0% | 0.1% | 0.0% |
| PhEtOH[7] | 0.4% | 0.4% | 0.4% | 0.4% | 0.5% | 0.4% | 0.4% | 0.4% | 0.2% | 0.4% |

[1] Sodium myristate (sodium tetradecanoate, NaC14): TCI Chemicals, Cat. # M0483 - AKA TCI NaM
[2] Water: Millipore, Burlington, MA (18 m-ohm resistance)
[3] Sodium chloride
[4] Ethanol (200 proof)
[5] FRESCOLAT ® MGA: Symrise
[6] WINSENSE ™ WS-5: Symrise
[7] PROTECTOL ® PE: 2-phenoxyethanol sold by BASF

TABLE 4

|  | Ex. 29 | Ex. 30 | Ex. 31 | Ex. 32 | Ex. 33 | Ex. 34 | Ex. 35 | Ex. 36 | Ex. 37 | Ex. 38 |
| --- | --- | --- | --- | --- | --- | --- | --- | --- | --- | --- |
| NaP[1] | 6.2% | 6.0% | 6.2% | 5.9% | 6.2% | 6.1% | 6.0% | 6.0% | 6.2% | 5.9% |
| Water[2] | 83.9% | 84.1% | 89.4% | 87.3% | 82.1% | 86.9% | 86.5% | 81.3% | 86.2% | 81.5% |
| NaCL[3] | 0.0% | 0.0% | 0.0% | 2.2% | 2.1% | 2.2% | 3.0% | 3.1% | 3.0% | 2.9% |
| EtOH[4] | 5.2% | 5.2% | 0.0% | 0.0% | 5.1% | 0.0% | 0.0% | 5.1% | 0.0% | 5.1% |
| MGA[5] | 4.3% | 4.1% | 4.0% | 4.1% | 4.1% | 4.2% | 4.0% | 4.2% | 4.0% | 4.1% |
| WS-5[6] | 0.0% | 0.0% | 0.0% | 0.0% | 0.0% | 0.0% | 0.0% | 0.0% | 0.0% | 0.0% |
| Perfume | 0.0% | 0.1% | 0.0% | 0.0% | 0.0% | 0.1% | 0.0% | 0.0% | 0.1% | 0.2% |
| PhEtOH[7] | 0.5% | 0.4% | 0.4% | 0.4% | 0.5% | 0.4% | 0.4% | 0.4% | 0.5% | 0.4% |

[1] Sodium palmitate (sodium hexadecanoate, NaC16): TCI Chemicals, Cat. # P0007 - AKA TCI NaP
[2] Water: Millipore, Burlington, MA (18 m-ohm resistance)
[3] Sodium chloride
[4] Ethanol (200 proof)
[5] FRESCOLAT ® MGA: Symrise
[6] WINSENSE ™ WS-5: Symrise
[7] PROTECTOL ® PE: 2-phenoxyethanol sold by BASF

TABLE 5

|  | Ex. 39 | Ex. 40 | Ex. 41 | Ex. 42 | Ex. 43 | Ex. 44 | Ex. 45 | Ex. 46 | Ex. 47 | Ex. 48 |
| --- | --- | --- | --- | --- | --- | --- | --- | --- | --- | --- |
| NaS[1] | 0.0% | 0.0% | 0.0% | 0.0% | 0.0% | 0.0% | 0.0% | 0.0% | 6.1% | 6.0% |
| NaS[2] | 6.1% | 6.0% | 6.1% | 6.3% | 6.3% | 6.2% | 6.5% | 6.2% | 0.0% | 0.0% |
| Water[3] | 86.3% | 83.8% | 85.1% | 89.9% | 83.7% | 87.6% | 81.6% | 84.9% | 81.2% | 86.5% |
| NaCL[4] | 1.0% | 1.0% | 2.3% | 3.3% | 3.1% | 2.1% | 2.9% | 3.2% | 3.2% | 3.0% |
| EtOH[5] | 2.0% | 4.2% | 1.9% | 0.0% | 2.1% | 2.1% | 3.9% | 5.2% | 5.1% | 0.0% |
| MGA[6] | 4.1% | 4.5% | 4.2% | 0.0% | 4.1% | 0.4% | 4.5% | 0.0% | 4.1% | 4.0% |
| WS-5[7] | 0.0% | 0.0% | 0.0% | 0.0% | 0.0% | 0.0% | 0.0% | 0.0% | 0.0% | 0.0% |

TABLE 5-continued

|  | Ex. 39 | Ex. 40 | Ex. 41 | Ex. 42 | Ex. 43 | Ex. 44 | Ex. 45 | Ex. 46 | Ex. 47 | Ex. 48 |
| --- | --- | --- | --- | --- | --- | --- | --- | --- | --- | --- |
| Perfume | 0.1% | 0.2% | 0.1% | 0.1% | 0.1% | 0.1% | 0.1% | 0.1% | 0.1% | 0.1% |
| PhEtOH[8] | 0.3% | 0.4% | 0.2% | 0.4% | 0.5% | 0.4% | 0.3% | 0.4% | 0.2% | 0.4% |
| Petrolatum[9] | 0.0% | 0.0% | 0.0% | 0.0% | 0.0% | 1.0% | 0.0% | 0.0% | 0.0% | 0.0% |

[1]Sodium stearate (sodium octadecanoate, NaC18): TCI Chemicals, Cat. # S0081 - AKA TCI NaS
[2]Sodium stearate (sodium octadecanoate, NaC18): Spectrum Chemicals, Cat. # S1447 - AKA Spect. NaS
[3]Water: Millipore, Burlington, MA (18 m-ohm resistance)
[4]Sodium chloride
[5]Ethanol (200 proof)
[6]FRESCOLAT ® MGA: Symrise
[7]WINSENSE ™ WS-5: Symrise
[8]PROTECTOL ® PE: 2-phenoxyethanol sold by BASF
[9]Petrolatum G2191 - Sonneborn

Examples 49 Through 54

Compositions in Table 6 are prepared using a heated mixing device. An overhead mixer (IKA Eurostar 40 Digital Overhead Mixer, Model #EURO-ST 40 D S001) and a 4-blade flat impeller is used. All preparations are heated on a hot plate (IKA C-Mag HS 7 Hot Plate; Model #C-MAG HS 7 S1), where the composition temperature is controlled with an accompanying probe (IKA ETS-D5 Temperature Probe; Model #ETS-D5).

The samples are prepared by adding water to a stainless-steel beaker. An overhead mixer is inserted into the water and started at a speed sufficient to induce vortex motion, while allowing the temperature to heat to 85° C., then the sodium chloride is added and stirred into solution. Sodium stearate is then added. Once the sodium stearate is dissolved into solution and the mix reaches 80° C., ethanol, a cooling sensate (L-menthol, FRESCOLAT® MGA, and WS-5), petrolatum, phenyloxyethanol, and perfume are added. The speed of mixer is increased to compensate, if needed, to continue the vortex motion. Mixing continues for five minutes, then the resulting mix is dispensed into molds and allowed to cool at room temperature.

TABLE 6

|  | Ex. 49 | Ex. 50 | Ex. 51 | Ex. 52 | Ex. 53 | Ex. 54 | Ex. 55 |
| --- | --- | --- | --- | --- | --- | --- | --- |
| NaS[1] | 0.0% | 6.0% | 6.0% | 6.0% | 6.0% | 6.0% | 6.0% |
| NaM[2] | 3.0% | 0.0% | 0.0% | 0.0% | 0.0% | 0.0% | 0.0% |
| Water[3] | 96.0% | 83.5% | 85.4% | 81.2% | 83.5% | 84.5% | 81.3% |
| NaCl[4] | 0.0% | 2.0% | 2.0% | 2.0% | 2.0% | 2.0% | 2.0% |
| EtOH[5] | 0.0% | 4.0% | 2.0% | 5.2% | 4.0% | 2.0% | 5.0% |
| L Menthol[6] | 0.0% | 0.0% | 0.0% | 0.0% | 0.0% | 0.0% | 0.0% |
| MGA[7] | 0.0% | 4.0% | 4.0% | 4.0% | 4.0% | 4.0% | 4.0% |
| WS-5[8] | 0.0% | 0.0% | 0.0% | 0.0% | 0.0% | 0.0% | 0.0% |
| Petrolatum[9] | 0.0% | 0.0% | 0.0% | 1.0% | 0.0% | 1.0% | 1.0% |
| Perfume | 0.0% | 0.1% | 0.1% | 0.1% | 0.1% | 0.1% | 0.3% |
| PhEtOH[10] | 0.4% | 0.4% | 0.4% | 0.4% | 0.4% | 0.4% | 0.4% |
| SYMDIOL ®[11] | 0.6% | 0.0% | 0.0% | 0.0% | 0.0% | 0.0% | 0.0% |
| Hardness (N) | Not Tested | 9.7 | 8.5 | 11.1 | Not Tested | 13.3 | Not Tested |
| Stability Temp. by DSC (° C.) | Not Tested | 43.2 | 41.7 | 44.2 | Not Tested | 42.4 | 42.1 |
| AP Expression (J/m3) | Not Tested | 2,933 | Not Tested | Not Tested | Not Tested | Not Tested | Not Tested |

[1]Sodium stearate (sodium octadecanoate, NaC18): Spectrum Chemicals, Cat. # S1447 - AKA Spect. NaS
[2]Sodium myristate (sodium tetradecanoate, NaC14): TCI Chemicals, Cat. # M0483 - AKA TCI NaM
[3]Water: Millipore, Burlington, MA (18 m-ohm resistance)
[4]Sodium chloride
[5]Ethanol (200 proof)
[6]L-Menthol: Sigma-Aldrich
[7]FRESCOLAT ® MGA: Symrise
[8]WINSENSE ™ WS-5: Symrise
[9]Petrolatum G2191: Sonneborn
[10]PROTECTOL ® PE: 2-phenoxyethanol sold by BASF
[11]SYMDIOL ® 68: Symrise

Examples 55 Through 61

Compositions in Table 7 are prepared using a heated mixing device. An overhead mixer and a 4-blade flat impeller is used. All preparations are heated in a 90° C. water bath (VWR, 7×7 stir pro), where the water bath temperature is controlled with an accompanying probe.

The examples are prepared by adding water to a 6 oz glass jar (VWR). Then, a high-speed homogenizer (IKA T 25 ULTRA-TURRAX®) is inserted into the water. The homogenizer is started at a speed sufficient to induce vortex motion and the speed is slowly increased, while xanthan gum is added. When the solution is free of clumps, mixing is stopped. The jar is removed and placed in the water bath, and the 4-blade impeller is inserted. Mixing is started at a speed sufficient to induce vortex motion. Then, sodium chloride is added and stirred into solution. Sodium palmitate is then added. Separately, pentaerythrityl tetraisostearate and a cooling sensate (L-menthol, FRESCOLAT® MGA, and FRESCOLAT® ML Nat.) are added to a 20 ml glass vial. This vial is placed in the water bath at 85° C. and periodically, manually swirled until homogenous. Once the sodium palmitate is dissolved into solution and the mix reaches 80° C., the contents of the 20 ml vial are poured into the glass jar. The speed of the mixer is increased to compensate, if needed, to continue the vortex motion. Mixing continues for five minutes, then the resulting mix is dispensed into stick molds and allowed to cool at room temperature.

TABLE 7

|  | Ex. 55 | Ex. 56 | Ex. 57 | Ex. 58 | Ex. 59 | Ex. 60 | Ex. 61 |
|---|---|---|---|---|---|---|---|
| NaM[1] | 4.8% | 5.0% | 5.0% | 5.0% | 5.1% | 3.6% | 5.0% |
| Water[2] | 70.1% | 83.7% | 88.2% | 88.2% | 90.3% | 91.7% | 88.2% |
| Xanthan[3] | 0.3% | 0.3% | 0.3% | 0.3% | 0.3% | 0.3% | 0.3% |
| PETI[4] | 5.8% | 2.5% | 1.0% | 1.0% | 1.0% | 1.1% | 1.0% |
| L-Menthol[5] | 15.6% | 5.0% | 0.0% | 2.0% | 0.0% | 0.0% | 0.0% |
| MGA[6] | 0.0% | 0.0% | 0.0% | 0.0% | 2.1% | 0.0% | 0.0% |
| NaCl[7] | 3.4% | 3.5% | 3.5% | 3.5% | 1.2% | 1.2% | 3.5% |
| ML Nat.[8] | 0.0% | 0.0% | 0.0% | 0.0% | 0.0% | 2.1% | 0.0% |
| NicoMentyl[9] | 0.0% | 0.0% | 2.0% | 0.0% | 0.0% | 0.0% | 0.0% |
| WS-5[10] | 0.0% | 0.0% | 0.0% | 0.0% | 0.0% | 0.0% | 2.0% |

[1]Sodium myristate (sodium tetradecanoate, NaC14): TCI Chemicals, Cat. # M0483
[2]Water: Millipore, Burlington, MA (18 m-ohm resistance)
[3]Xanthan Gum: CP Kelco
[4]Pentaerythrityl Tetraisostearate: Custom Synthesis, LLC
[5]L-Menthol: Sigma-Aldrich
[6]FRESCOLAT ® MGA: Symrise
[7]Sodium chloride
[8]FRESCOLAT ® ML Nat.: Symrise
[9]NICOMENTHYL ®: menthyl nicotinate sold by Multichem R&D
[10]WINSENSE ™ WS-5: Symrise

Examples 62 Through 71

The compositions in Table 8 are prepared using a heated mixing device. An overhead mixer (IKA Works Inc, Wilmington, NC, model RW20 DMZ) and a three-blade impeller design are assembled. All preparations are heated on a heating-pad assembly (VWR, Radnor, PA, 7×7 CER Hotplate, cat. no. NO97042-690), where heating is controlled with an accompanying probe.

The solutions are prepared by adding water and sodium myristate to a stainless-steel beaker (Thermo Fischer Scientific, Waltham, MA). The beaker is placed on the heated mixing device. The overhead mixer is placed in the beaker and set to rotate at 100 rpm. The heater is set to 80° C. The preparation is heated to 80° C. The solution is then cooled down to 60° C., at which point L-menthol, ethanol, WS-5, and FRESCOLAT® MGA are added and mixed until thoroughly dissolved. Sodium chloride is added and further mixed until thoroughly dissolved. The solution is then divided into three 60 g plastic jars (Flak-Tech, Max 60 Cup Translucent, Cat #501 222t): one jar is filled to 50 ml and two jars are filled to 25 ml. The samples are cooled at room temperature 25° C. (±3° C.) until solid. Firmness measurements are made on the 50 ml samples using the FIRMNESS TEST METHOD

TABLE 8

|  | Ex. 62 | Ex. 63 | Ex. 64 | Ex. 65 | Ex. 66 | Ex. 67 | Ex. 68 | Ex. 69 | Ex. 70 | Ex. 71 |
|---|---|---|---|---|---|---|---|---|---|---|
| NaM[1] | 6.0% | 3.0% | 6.0% | 6.0% | 6.0% | 6.0% | 6.0% | 6.0% | 9.8% | 10.0% |
| Water[2] | 86.6% | 96.2% | 87.6% | 83.1% | 90.6% | 89.5% | 93.5% | 92.0% | 84.9% | 85.1% |
| NaCl[3] | 0.0% | 0.0% | 1.0% | 6.0% | 0.0% | 0.0% | 0.0% | 0.0% | 0.0% | 0.0% |
| EtOH[4] | 6.0% | 0.0% | 4.0% | 4.0% | 2.0% | 4.0% | 0.0% | 2.0% | 3.9% | 4.0% |
| L Menthol[5] | 0.2% | 0.1% | 0.2% | 0.1% | 0.2% | 0.1% | 0.0% | 0.0% | 0.2% | 0.2% |
| MGA[6] | 1.1% | 0.7% | 1.1% | 0.8% | 1.1% | 0.4% | 0.0% | 0.0% | 1.1% | 0.8% |
| WS-5[7] | 0.0% | 0.0% | 0.0% | 0.0% | 0.0% | 0.0% | 0.5% | 0.0% | 0.0% | 0.0% |
| Firmness | 0.4N | 2.8N | 8.2N | 10.6N | 14.6N | 21.2N | 24.2N | 27.0N | 31.5N | 41.1N |

[1]Sodium myristate (sodium tetradecanoate, NaC14): TCI Chemicals, Cat. # M0483 - AKA TCI NaM
[2]Water: Millipore, Burlington, MA (18 m-ohm resistance)
[3]Sodium chloride
[4]Ethanol (200 proof)
[5]L-Menthol: Sigma-Aldrich
[6]FRESCOLAT ® MGA: Symrise
[7]WINSENSE ™ WS-5: Symrise Experimental Consumer Data Forty consumers are asked to rate their level of satisfaction with their current solutions for treating the symptoms of hot flashes on a scale of 1 to 5, with one being the most dissatisfied and five being the most satisfied. These consumers report that their current solutions include using fans, using cold water, or layering clothing to treat the symptoms of hot flashes, and the consumers return an average satisfaction rating of 2.4 for their current solutions. Thirteen consumers are provided the composition of Example 49 from Table 6 and rate their satisfaction as 2.5. This suggests that the composition of Example 49 provides about the same level of satisfaction as the consumers' current solutions. Example 50 is tested with nine consumers and consumers rate their average satisfaction as 4.5, suggesting that the composition of Example 50 provides greater satisfaction than the consumers' current solutions. The composition of Example 50 contains ethanol and a cooling sensate, whereas the composition of Example 49 does not contain either ethanol or a cooling sensate. The composition of Example 49 provides only evaporative cooling via water. In the composition of Example 50, the addition of ethanol, which provides evaporative cooling, and the cooling sensate increases consumer satisfaction.

Combinations

A. A personal care composition comprising:
   i) from about 1% to about 12%, preferably from about 2 to about 10%, more preferably from about 4% to about 8%, by weight of a salt of a fatty acid containing from about 13 to about 20 carbon atoms,
   ii) from about 70% to about 99.5%, preferably from about 75% to about 95%, more preferably from about 80% to about 92.5%, by weight water,
   iii) from 0.5% to about 15%, preferably from about 1% to about 10%, more preferably from about 2% to about 8%, by weight of an alcohol selected from the group consisting of methanol, ethanol, propanol, isopropanol, and mixtures thereof, and
   iv) from about 0.1% to about 25%, preferably from about 0.25% to about 20%, more preferably from about 0.5% to about 15%, by weight of a sensate, preferably a cooling sensate.
B. The composition of paragraph A, where the salt of a fatty acid is a metal salt, preferably a metal salt selected from the group consisting of sodium, potassium, magnesium, calcium, and lithium, more preferably a sodium salt.
C. The composition of any one of the preceding paragraphs, where the salt of a fatty acid is selected from the group consisting of stearate, palmitate, myristate, tridecanoate, pentadecanoate, heptadecanoate, and nanodecanoate, preferably selected from the group consisting of stearate, palmitate, and myristate, more preferably selected from the group consisting of sodium stearate, sodium palmitate, and sodium myristate.
D. The composition of any one of the preceding paragraphs, where the sensate is selected from the group consisting of menthol, a carboxamide, a menthol derivative, and combinations thereof, preferably selected from the group consisting of a carboxamide, a menthol derivative, and combinations thereof.
E. The composition of any one of the preceding paragraphs, where the sensate is selected from the group consisting of menthol, 3-1-menthoxypropane-1,2-diol, menthyl lactate, N,2,3-trimethyl-2-isopropylbutanamide, N-ethyl-p-menthan-3-carboxamide, N-(4-cyanomethylphenyl)-ρ-menthanecarboxamide, and combinations thereof, preferably selected from the group consisting of 3-1-menthoxypropane-1,2-diol, menthyl lactate, N,2,3-trimethyl-2-isopropylbutanamide, N-ethyl-p-menthan-3-carboxamide, N-(4-cyanomethylphenyl)-ρ-menthanecarboxamide, and combinations thereof.
F. The composition of any one of the preceding paragraphs, where the sensate stimulates TRPM8 activity.
G. The composition of any one of the preceding paragraphs, where the sensate blocks TRPV1 activity, TRPA1 activity, or both.
H. The composition of any one of the preceding paragraphs, where the sensate is a natural oil extract, preferably selected from the group consisting of peppermint oil, anise oil, sweet birch oil, spearmint oil, clove bud oil, eucalyptus oil, and mixtures thereof, more preferably selected from the group consisting of peppermint oil, spearmint oil, clove bud oil, eucalyptus oil, and mixtures thereof.
I. The composition of any one of the preceding paragraphs, where the sensate is substantially free of menthol.
J. The composition of any one of the preceding paragraphs, where the composition further comprises a component selected from the group consisting of a thickening agent, preferably xanthan gum, a preservative, a skin care active, a perfume, an acid, a base, a salt, a chelant, a solvent, a surfactant, a polymer, a buffer, a colorant, and mixtures thereof, preferably selected from the group consisting of a thickening agent, preferably xanthan gum, a preservative, a skin care active, a perfume, a salt, and mixtures thereof.

K. The composition of any one of the preceding paragraphs, where the composition further comprises a surfactant selected from the group consisting of anionic surfactants, nonionic surfactants, cationic surfactants, zwitterionic surfactants, and amphoteric surfactants.

L. The composition of any one of the preceding paragraphs, where the composition is a solid at 25° C. and 1 ATM.

M. The composition of any one of the preceding paragraphs, where the composition has a firmness between about 0.1 N to about 50.0 N, preferably between about 0.5 N to about 25.00 N, more preferably between about 1 N and about 20.0 N, as determined by the FIRMNESS TEST METHOD.

N. The composition of any one of the preceding paragraphs, where the composition has a thermal stability greater than about 40° C., preferably greater than about 45° C. as determined by the THERMAL STABILITY TEST METHOD.

O. The composition of any one of the preceding paragraphs, where the composition has a liquid expression from about 300 J m-3 to about 9,000 J m-3, preferably from about 1,000 J m-3 to about 7,000 J m-3, more preferably from about 2,000 J m-3 to about 5,000 J m-3, as determined by the AQUEOUS SOLUTION EXPRESSION TEST METHOD.

P. A method of treating keratinous tissue comprising the steps of:
  i) providing a composition of any one of the preceding paragraphs;
  ii) applying the composition, preferably a safe and effective amount of the composition, to at least a portion of keratinous tissue, where the keratinous tissue is skin or hair;
  iii) and optionally leaving the composition on the keratinous tissue for at least about 60 seconds, preferably for at least several hours, more preferably until the next application of the composition.

Q. A method of treating hot flashes, the method comprising the steps of:
  i) providing to a user in need thereof a composition comprising from about 0.01% to about 12%, preferably from about 1% to about 10%, more preferably from about 2% to about 9%, by weight of a salt of a fatty acid containing from about 13 to about 20 carbon atoms, from about 70% to about 99.5%, preferably from about 75% to about 98%, more preferably from about 80% to about 97%, by weight water;
  ii) applying the composition, preferably a safe and effective amount of the composition, to at least a portion of keratinous tissue of the user, where the keratinous tissue is skin or hair;
  iii) and optionally leaving the composition on the keratinous tissue for at least about 60 seconds, preferably for at least several hours, more preferably until the next application of the composition.

R. The method of paragraph Q, where from about 0.1 g to about 5 g, more preferably from about 0.2 g to about 4 g, more preferably from about 0.3 g to about 3 g of the composition is applied to the keratinous tissue per day.

S. The method of paragraph Q, where the composition provides upon use an immediate onset of a cooling sensation and the cooling sensation lasts from about 5 seconds to about 30 minutes.

T. The method of paragraph Q, where the composition further comprises from 0.5% to about 15%, preferably from about 1% to about 10%, more preferably from about 2% to about 8%, by weight of an alcohol selected from the group consisting of methanol, ethanol, propanol, isopropanol, and mixtures thereof, and from about 0.1% to about 25%, preferably from about 0.25% to about 20%, more preferably from about 0.5% to about 15%, by weight of a sensate.

U. The method of paragraph Q, where the keratinous tissue is on one of the following body parts: the lips, the face, the neck, the arm, preferably the underarm, the upper and/or forearm, or a combination thereof, the wrist, the hands, the chest, the back, the loin, the leg, the thigh, the abdomen, or a combination thereof.

V. The method of paragraph Q, where the composition is applied to the portion of keratinous tissue of the user prior to a hot flash, during a hot flash, after a hot flash, or a combination thereof.

W. The method of paragraph Q, where the composition is applied to the portion of keratinous tissue of the user prior to sleeping.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A personal care composition comprising:
  i.) from about 1% to about 12% by weight of a salt of a fatty acid containing from 13 to about 20 carbon atoms,
  ii.) from about 70% to about 99.5% by weight water,
  iii.) from 0.5% to about 15% by weight of an alcohol selected from the group consisting of methanol, ethanol, propanol, isopropanol, and mixtures thereof, and
  iv.) from about 0.1% to about 25% by weight of a cooling sensate;
  wherein:
    the salt of a fatty acid functions as a crystallizing agent to form a crystalline mesh with voids;
    the voids comprise aqueous solution; and the aqueous solution is expressed when the personal care composition is compressed above a critical stress;

wherein the personal care composition has a liquid expression from about 300 J m-3 to about 9,000 J m-3, as determined by the AQUEOUS SOLUTION EXPRESSION TEST METHOD at room temperature (25±3° C.); and wherein the composition has a firmness between about 0.1 N to about 50.0 N, as determined by the FIRMNESS TEST METHOD at room temperature (25±3° C.).

2. The personal care composition according to claim 1, wherein the salt of a fatty acid is a metal salt selected from the group consisting of sodium, potassium, magnesium, calcium, and lithium.

3. The personal care composition according to claim 1, wherein the salt of a fatty acid is selected from the group consisting of stearate, palmitate, myristate, tridecanoate, pentadecanoate, heptadecanoate, and nonadecanoate.

4. The personal care composition according to claim 1, wherein the sensate is selected from the group consisting of menthol, a carboxamide, a menthol derivative, and combinations thereof.

5. The personal care composition according to claim 1, wherein the sensate is selected from the group consisting of menthol, 3-l-menthoxypropane-1,2-diol, menthyl lactate, N,2,3-trimethyl-2-isopropylbutanamide, N-ethyl-p-menthan-3-carboxamide, N-(4-cyanomethylphenyl)-p-menthanecarboxamide, and combinations thereof.

6. The personal care composition according to claim 1, wherein the sensate stimulates Transient Receptor Potential Cation Channel Subfamily M Member 8 (TRPM8) activity.

7. The personal care composition according to claim 1, wherein the sensate blocks Transient Receptor Potential Vanilloid 1 (TRPV1) activity, Transient Receptor Potential Ankyrin 1 (TRPA1) activity, or both.

8. The personal care composition according to claim 1, wherein the sensate is a natural oil extract selected from the group consisting of peppermint oil, anise oil, sweet birch oil, spearmint oil, clove bud oil, eucalyptus oil, and mixtures thereof.

9. The personal care composition according to claim 1, wherein the sensate is substantially free of menthol.

10. The personal care composition according to claim 1, wherein the composition further comprises a component selected from the group consisting of a thickening agent, a preservative, a skin care active, a perfume, an acid, a base, a salt, a chelant, a solvent, a surfactant, a polymer, a buffer, a colorant, and mixtures thereof.

11. The personal care composition according to claim 1, wherein the composition further comprises a surfactant selected from the group consisting of anionic surfactants, nonionic surfactants, cationic surfactants, zwitterionic surfactants, and amphoteric surfactants.

12. The personal care composition according to claim 1, wherein the composition is a solid at 25° C. and 1 ATM.

13. The personal care composition according to claim 1, wherein the composition has a thermal stability greater than about 40° C., as determined by the THERMAL STABILITY TEST METHOD starting at room temperature (25 ±3° C.) and using a ramp of 1.00° C./min to 90.00° C.

14. The personal care composition according to claim 1, wherein the composition comprises from about 2 to about 10% by weight of a salt of a fatty acid containing from about 13 to about 20 carbon atoms, from about 75% to about 95% by weight water, from about 1% to about 10% by weight of an alcohol selected from the group consisting of methanol, ethanol, propanol, isopropanol, and mixtures thereof, and from about 0.25% to about 20% by weight of a cooling sensate.

15. A method of treating hot flashes, the method comprising the steps of:

providing to a user in need thereof a composition comprising from about 0.01% to about 12% by weight of a salt of a fatty acid containing from 13 to 20 carbon atoms, from about 70% to about 99.5% by weight water; wherein:

the salt of a fatty acid functions as a crystallizing agent to form a crystalline mesh with voids;

the voids comprising aqueous solution; and applying the composition to at least a portion of keratinous tissue of the user by compressing the composition above a critical stress to express the aqueous solution, wherein the keratinous tissue is skin or hair; and leaving the composition on the keratinous tissue for at least about 60 seconds;

wherein the personal care composition has a liquid expression from about 300 J m-3 to about 9,000 J m-3, as determined by the AQUEOUS SOLUTION EXPRESSION TEST METHOD at room temperature (25±3° C.); and wherein the composition has a firmness between about 0.1 N to about 50.0 N, as determined by the FIRMNESS TEST METHOD at room temperature (25±3° C.).

16. The personal care composition according to claim 1, where the crystalline mesh is formed of particles in which the length of the particles in a direction of their longest axis is greater than 10 times the length of the particles in any orthogonal direction.

17. The personal care composition according to claim 1, wherein the salt of a fatty acid has a Single Purity, Ps, of greater than 0.5.

18. The personal care composition according to claim 1, wherein the-salt of a fatty acid has an Optimal Purity, Po, of greater than 0.4.

* * * * *